(12) United States Patent
Rehberger et al.

(10) Patent No.: US 7,618,640 B2
(45) Date of Patent: *Nov. 17, 2009

(54) **METHOD AND COMPOSITION FOR REDUCING *E. COLI* DISEASE AND ENHANCING PERFORMANCE**

(75) Inventors: Thomas G. Rehberger, Wauwatosa, WI (US); Dorrie Sue Jordan-Parrott, El Reno, OK (US)

(73) Assignee: Agtech Products, Inc., Maukesha, WI (US)

( * ) Notice: Subject to any disclaimer, the term of this patent is extended or adjusted under 35 U.S.C. 154(b) by 218 days.

This patent is subject to a terminal disclaimer.

(21) Appl. No.: 11/129,767

(22) Filed: May 13, 2005

(65) Prior Publication Data

US 2005/0255092 A1 Nov. 17, 2005

Related U.S. Application Data

(60) Provisional application No. 60/571,193, filed on May 14, 2004.

(51) Int. Cl.
*A61K 39/02* (2006.01)
*G01N 33/53* (2006.01)
(52) U.S. Cl. ..................... 424/200.1; 435/7.1
(58) Field of Classification Search ............... 424/200.1
See application file for complete search history.

(56) References Cited

U.S. PATENT DOCUMENTS

| | | | |
|---|---|---|---|
| 2,906,622 | A | 9/1959 | Lewis |
| 2,942,977 | A | 6/1960 | Lewis et al. |
| 4,820,531 | A | 4/1989 | Tomes |
| 4,919,936 | A | 4/1990 | Iwanami et al. |
| 5,478,557 | A | 12/1995 | Nisbet |
| 5,482,723 | A | 1/1996 | Sasaki |
| 5,507,250 | A | 4/1996 | Reddy |
| 5,540,924 | A | 7/1996 | Onishi |
| 5,703,040 | A | 12/1997 | Iandolo |
| 5,718,894 | A | 2/1998 | Mann et al. |
| 5,830,993 | A | 11/1998 | Blecha |
| 5,840,318 | A | 11/1998 | Marshall |
| 5,879,719 | A | 3/1999 | Valentine |
| 5,945,333 | A | 8/1999 | Rehberger |
| 5,964,187 | A | 10/1999 | Willis |
| 5,965,128 | A | 10/1999 | Doyle |
| 6,008,195 | A | 12/1999 | Selsted |
| 6,156,355 | A | 12/2000 | Shields, Jr. |
| 6,207,411 | B1 | 3/2001 | Ross |
| 6,221,650 | B1 | 4/2001 | Rehberger |
| 6,346,422 | B1 | 2/2002 | Butty et al. |
| 6,410,016 | B2 | 6/2002 | Maruta |
| 7,247,299 | B2 | 7/2007 | Lin et al. |
| 2002/0018770 | A1 | 2/2002 | Maruta |
| 2003/0099624 | A1 | 5/2003 | Porubcan |
| 2004/0170617 | A1 | 9/2004 | Finegold |
| 2005/0255092 | A1 | 11/2005 | Rehberger |
| 2007/0202088 | A1 | 8/2007 | Baltzley et al. |

FOREIGN PATENT DOCUMENTS

WO 2004104175 A2 5/2004

OTHER PUBLICATIONS

"Table of contents" 'Online! 2004, p. 1-4, Internet, http://www.fass.org/2004/abstracts/.
"Nonruminant Nutrition: weanling Pigs—additives" 'Online! 2004, p. 25-28, Internet, http://www.fass.org/2004/abstracts/25.PDF.
"For immediate release" 'Online! Jan. 13, 2005, p. 1-2, Internet, http://www.agtechproducts.com/press/DSM_Market_MicroSource.pdf.
"Watt Feed E-news Feb. 8, 2005" 'Online! , p. 1-6, Internet, http://www.wattnet.com/Newsletters/feed/htm/FEBFEED05.htm.
Agtech Products, Inc., "DSM Nutritional Products, Inc. to market Agtech Products, Inc.'s MicroSource "S" and "8818" direct-fed microbial products for swine," Jan. 13, 2005 Press Release found at www.agtechproducts.com/press/DS.
Awad, M M et al, "Synergistic effects of alpha-toxin and perfringolysin O in *Clostridium perfringens*-mediated gas gangrene."
Banach, S et al, "Prevalence, distribution and diversity of pathogenic *E. coli* in commercial turkey poult production," Presented at the Poultry Science Association Annual Meeting, Madison, WI, Jul. 2003.
Banach, S et al, "Prevalence, distribution and diversity of pathogenic *E. coli* in commerical turkey poult production," Poster #337, presented at the Poultry Science Association Annual Meeting, Madison, WI, Jul. 2003.
Bertschinger, H U, "*Escherichia coli* infections," Diseases of Swine 8th Ed., Chap. 32, pp. 431-454, 1999.
Blood, D C, "Diseases caused by bacteria," Veterinary Medicine, 7th Ed., Bailliere, pp. 637-640, 1989.
Brosius, J et al, "Complete nucleotide sequence of a 16S ribosomal RNA gene from *Escherichia coli*," Proc Natl Acad Sci USA 75(10:4801-4805, Oct. 1978.
Carr, D et al, "Excessive mortality in market-age turkeys associated with cellulitis," Avian Disease 40:736-741, 1996.
Dean-Nystrom, E and Bartels-Morozov, D, "Edema disease: a re-emerging problem?," Am Assoc of Swine Veterinarians, pp. 223-224, 2001.
Donald, J, "Treating poultry house floors to improve poor performance," The Poultry Engineering, Economics & Management Newsletter, Issue No. 23, 4 pgs, May 2003.

(Continued)

*Primary Examiner*—Robert Mondesi
*Assistant Examiner*—Khatol Shahnan-Shah
(74) *Attorney, Agent, or Firm*—Whyte Hirshboeck Dudek S.C.

(57) ABSTRACT

*Bacillus* strains that inhibit pathogenic swine *E. coli* and/or improve performance are provided. Inhibition of pathogenic swine *E. coli* decreases *E. coli* disease. At least one strain enhanced swine performance by improving average daily gain, feed efficiency, and feed intake. Preferred *Bacillus* strains are of species that are included on the GRAS list. *Bacillus* species are sporeformers and therefore are highly stable and can be fed to swine.

23 Claims, 19 Drawing Sheets

OTHER PUBLICATIONS

Francis, D, "Post-weaning *E. coli*-diagnosis, treatment, control, and its effect on subsequent growth performance," Am Assoc of Swine Veterinarians, 495-499, 2004.

Grimes, J L et al, "Heat treatment of turkey litter for reuse as bedding," Int J of Poultry Science 2(5):287-292, 2003.

Hofacre, C L et al, "Subcutaneous Clostridial infection in broilers," Case Report, Avian Diseases vol. 30(3):620-622, 1986.

Karunakaran, D et al, "Use of antibiotics and its impact on gut microflora in turkeys,"Am Avian Path, Philadelphia, PA, Aug. 2004.

Karunakaran, D, "Microbiological challenges of commercial turkey flocks and methods of control," Poster #PP51 presented at AAAP Symposium on Poultry Vaccines and Vaccination Practices, Jul. 15-17, 2002.

Kennedy, C et al, "The A-toxin of *Clostridium septicum* is essential for virulence," Molecular Microbiology, 57(5):1357-1366, 2005.

Lu, J et al, "Diversity and succession of the intestinal bacterial community of the maturing broiler chicken," Applied and Environmental Microbiology, 60(11):6816-6824, Nov. 2003.

Marquardt, R et al, "Passive protective effect of egg-yolk antibodies against entertoxigenic *Escherichia coli* K88+ infection in neonatal and early-weaned piglets," FEMS Immunology and Med Microbiology 23:283-288, 1999.

Muyzer, G et al, "Profiling of complex microbial populations by denaturing gradient gel electrophoresis analysis of polymerase chain reaction-amplified genes coding for 16S rRNA,"Applied and Environmental Microbiology, 59(3):695-700, Mar. 1993.

Nagy, G et al, "Genetic diversity among *Escherichia coli* isolates carrying f18 gene from pigs with porcine postweaning diarrhea and edema disease," J Clinical Microbiology 37:5:1642-1645, May 1999.

Parrott, D et al, "Molecular typing of hemolytic *Escherichia coli* isolated from swine," Paper 385 (1 pg), Intl Pig Vet Soc, 2002.

Patterson, J A, and Burkholder, K M, "Application of prebiotics and probiotics in poultry production," Poultry Science 82:627-631, 2003.

Pyne, E et al, "Prevalence and genetic diversity of *Clostridium perfringers* isolated from commerical turkey houses," Abstract #432 in Abstracts of Papers.

Rehberger, T, "Genome analysis of *Propionibacterium freudenreichii* by pulsed-field gel electrophoresis," Current Microbiology 27(1):21-25, Jul. 1993 (abstract).

Sambrook, 3d Ed., 2001 (reference book, no specific pages cited or copy provided).

Snoeyenbos, G H, "Protecting chicks and poults from *Salmonellae* by oral administration of "normal" gut microflora," Avian Diseases 22(2)::273-287, 1977.

Wiard, T et al, "The effect of a biological litter treatment on *Salmonella* prevalence in turkey breeder flock litter," Poultry Science 80:127 (Suppl. 1):1-4, 2001.

Wiard, T et al, "Application of plating enumerations and denaturing gradient gel electrophoresis to study turkey poult gastrointestinal tract bacterial diversity," (4 pgs) presented at the Poultry Science Assoc meeting, Madison, WI 2003.

Wiard, T et al, "Application of plating enumerations and denaturing gradient gel electrophoresis to study turkey poult gastrointestinal tract bacterial diversity," Poster #244 and its abstract, presented at the Poultry Science Assoc meeting, Madison, WI 2003.

Willoughby, D H et al, "Periodic recurrence of gangernous dermatitis associated with *Clostridium septicum* in a broiler chicken operation," J Vet Diagn Invest 8:259-261, 1996.

Wills, "*Escherichia coli* postweaning diarrhea," Vet Clinics N Am, pp. 138-140, 2000.

Zhu, X Y, "16S rRNA-based analysis of microbiota from the cecum of broiler chickens," Applied and Environmental Microbiology, 68(1):124-137, Jan. 2002.

Zoetendal, E G et al, Molecular ecological anaylsis of gastrointestinal microbiota: a review, J of Nutrition pp. 465-472, 2004.

NCBI gene bank accession #X73447.

NCBI gene bank accession #M59107.

Fritts, C A et al, "*Bacillus subtilis* C-3102 (Calsporin) improves live performance and microbiological status of broiler chickens," Applied Poultry Scienc, Inc., 9:149-155, 2000.

La Ragione R M et al, "*Bacillus subtilis* spores competitively exclude *Escherichia coli* O78:K80 in poultry," Vet Microbiol 79:133-142, 2001.

Wattiau, P et al, "A PCR test to identify *Bacillus subtilis* and closely related species and its application to the monitoring of wastewater biotreatment," Appl Microbiol Biotechnol 56:816-819, 2001.

Awad, M M et al, "Synergistic effects of alpha-toxin and Perfringolysin O in Clostridium perfringens-mediated gas gangrene," Infection and Immunity, 69(12):7904-7910, 2001.

Bosworth, B T and T A Casey, "Identification of toxin and pilus genes in porcine *Escherichia coli* using polymerase chain reaction (PCR) with multiple primer pairs," 97th General Meeting, Am. Soc. Microbiol. Abstract B-509, p. 116, (1997).

Cooper, V, "Diagnosis of neonatal pig diarrhea," Vet Clinics N Am Food Animal Practice, 16(1):117-161 (2000).

Roe, S, "Protein purification techniques," 2d Ed., Oxford U. Press, 172-175 (2001).

Marsh, T. et al, "Terminal restriction fragment length polymorphism analysis web-based research tool for microbial community analysis," Appl Environ Microbiol (2000) 66:3616-3620.

Maxwell, Jr., C. V. et al, "Feeding Weanling Pigs. In: Austin J. Lewis and Lee L. Southern (Ed.)," Swine Nutrition 2nd Edition. (2001) p. 691-717.

Mccracken, B. A. et al, "Diet-dependent and diet-independent metabolic responses underlie growth stasis of pigs at weaning," J. Nutr. (1995) 125, 2838-2845.

Mcdonough, S. P., "Enteric pathogens in intensively reared veal calves," Am. J. Vet. Res. (1994) 55(11):1516-1520.

Mcmillan, K., "Foal pneumonia: An Illinois survey," An Health and Nutrit 34 (1986).

Morrill, J. L. et al, "Plasma proteins and a probiotic as ingredients in milk replacer," J. Dairy Sci. (1995) 78:902-907.

Mouricout, M. A. et al, "Inhibition of mannose-resistant haemagglutination of sheep erythrocytes by enterotoxigenic *Escherichia coli* in the presence of plasma glycoprotein glycans," Fems Microbiol. Lett. (1986) 37:145-149.

Muir, L. A. et al, "Prevention of induced lactic acidosis in cattle by thiopeptin," J. Anim. Sci. (1981) 52:635.

Niilo, L., "Clostridium perfringens in animal disease: a review of current knowledge," Can. Vet. J. (1980) 21:141-148.

Nollet, H. et al, "Protection of just weaned pigs against infection with F18+ *Escherichia coli* by non-immune plasma powder," Vet. Microbiol. (1999) 65:37-45.

Owens, F. N. et al, "Acidosis in cattle: a review," J. Anim. Sci. (1998) 76:275-286.

Perez-Bosque, A. et al, "Dietary plasma protein affects the immune response of weaned rats challenged with S. aureus," Superantigen B. J. Nutr. (2004) 134:2667-2672.

Power, E. G., "RAPD typing in microbiology—a technical review," J. Hosp. Infect. (1996) 34(4):247-265.

Roche, K. C. et al, "Transforming growth factor beta-1 ameliorates intestinal epithelial barrier disruption by *Cryptosporidium parvum* in the absence of mucosa T lymphocytes," Infect. Immun. (2000) 68:5635-5644.

Slyter, L.L., "Influence of acidosis on rumen function," J. Anim. Sci. (1976) 43:910.

Songer, J. G., "Clostridial enteric diseases of domestic animals," Clinical Microbiology Reviews (1996) 9(2):216-234.

Stable Fresh TM 1:3 concentrate, "An all natural USDA approved concentrate that eliminates stall odors for just pennies per day, per stall," Sterling Creek Enterprises (2 pgs).

Tam, N. K. M. et al, "The intestinal life cycle of *Bacillus subtilis* and close relatives," J. Bacteriol. (2006) 188:2692-2700.

Tang, M. et al, "Effect of segregated early weaning on postweaning small intestinal development in pigs," J. Anim. Sci. (1999) 77:3191.

Tanner, M. K. et al. "Respiratory and environmental effects of recycled phone book paper versus sawdust as bedding for horses," J Eq Vet Sci (1998) 468-476.

Tannock, G. W., "A special fondness for lactobacilli," Appl. Environ, Microbiol. (2004) 70:3189-3194.

Teo et al., "Applied & Environmental Microbiology," (Aug. 2005) vol. 71, 8:4185-4190.

Timmerman, H. M. et al, "Health and growth of veal calves fed milk replacers with or without probiotics," J. Dairy Sci. (2005) 88:2154-2165.

Torrallardona, D. et al, "Effect of fishmeal replacement with spray-dried plasma and colistin on intestinal structure, intestinal microbiology, and performance of weanling pigs challenged with *Escherichia coli* K99," J. Anim. Sci. (2003) 81:1220-1226.

Van Dijk, A. et al, "Growth performance of weanling pigs fed spray-dried animal plasma: a review," Livestock Production Science (2001a) 68:263-274.

Van Dijk, A. et al, "Growth performance and health status in weanling piglets fed spray-dried porcine plasmas under typical Northern European conditions," J. Anim. Physiol. Anim. Nutr. (Berl). (2002b) 86:17-25.

Vance, H. N., "A survey of the alimentary tract of cattle for *Clostridium perfringens*," Can. J. Comp. Med. Vet. Sci. (1967) 31:260-264.

Williams, J. G. et al, "DNA polymorphisms amplified by arbitrary primers are useful as genetic markers," Nucleic Acids Res. (1990) 18:6531-6535.

Wilson, M, "Segregated early weaning," Pig Lett. (1995) 15:17-20.

Wistuba et al, "Influence of fish oil supplementation on growth and immune system characteristics of cattle," J. Anim. Sci. (2005) 83:1097-1101.

Wu, X. Y. et al, "Characterization of mesophilic bacilli in feces of feedlot cattle," J. Appl. Microbiol. (2007) 102:872-879.

Yang, H. et al, "Effect of adding a bacillus based direct fed microbial on performance of nursery pigs fed diets with or without antibiotics," J. Anim. Sci. (2003).

Yang, W., "Effects of direct-fed microbial supplementation on ruminal acidosis, digestibility, and bacterial protein synthesis in continuous culture," Animal Feed Science and Technology, (2004) 114(4): 179 -193.

International Search Report and the Written Opinion of the International Searching Authority, or the Declaration mailed Dec. 9, 2005 for PCT/US2005/017141, filed on May 13, 2005.

Non-Final Office Action mailed May 13, 2009 for U.S. Appl. No. 11/565,474, filed on Nov. 30, 2006.

Notice of Allowance, mailed Apr. 10, 2009 for U.S. Appl. No. 11/129,767, filed on May 13, 2005.

Final Office Action mailed Jan. 22, 2009 for U.S. Appl. No. 11/129,767, filed on May 13, 2005.

Non-Final Office Action mailed Feb. 5, 2008 for U.S. Appl. No. 11/129,767, filed on May 13, 2005.

International Search Report and the Written Opinion of the International Searching Authority, or the Declaration mailed Dec. 6, 2009 for PCT/US2009/40920, filed on Apr. 17, 2000.

Abe, F et al, "Effect of administration of Bifidobacteria and lactic acid bacteria to newborn calves and piglets," J. Dairy Sci. (1995) 78:2838-2846.

Adami , A. et al, "Piglets fed from birth with the probiotic *Bacillus coagulans* as additive: zootechnical and microbiological aspects," Ann Microbiol Enzimol (1997) 47: 139-149.

Allison, M .J. et al, "Grain overload in cattle and sheep: Changes in microbial populations in the cecum and rumen," Amer. J. Vet Res. (1975) 36:181.

Baker, A. et al, "Development of a *Bacillus subtilis* product for a large commercial swine farm to reduce *Clostridium perfringens* and *Clostridium difficile* in neonatal pigs," J. Anim. Sci. (2007) 85(suppl. 1):102.

Baker, G. C. et al, "Review and re-analysis of domain-specific 16S primers," Journal of Microbiological Methods (2003) 55:541-555.

Barbosa, et al, "Applied and Environmental Microbiology," (Feb. 2005) vol. 71, 2:968-978.

Bembridge et al. "CD45RO expression on bovine T cells: relation to biological function," Immunology, (1995) 86:537-544.

Bikker, P. et al, "The influence of diet composition and an antimicrobial growth promoter on the growth response of weaned piglets to spray dried animal plasma." Livestock Prod. Sci. (2004) 86:201-208.

Billington et al., "Clostridium perfringens Type E animal enteritis isolates with highly conserved, silent enterotoxin gene sequences," Infect Immun. (1998) 66(9):4531-4536.

Bosi, P. et al, "Effect of different spray dried plasmas on growth, ileal digestibility, nutrient deposition, immunity and health of early-weaned pigs challenged with *E. coli* K88," Asian-Aust J. Anim. Sci. (2001) 14:1138-1143.

Bosi, P. et al, "Spray-dried plasma improves growth performance and reduces inflammatory status of weaned pigs challenged with enterotoxigenic *Escherichia coli* K88," J. Anim. Sci. (2004) 82:1764-1772.

Brown, D. C. et al, "The influence of different management systems and age on intestinal morphology, immune cell Numbers and mucin production from goblet cells in post-weaning pigs," Vet. Immunol. Immunopath (2006a) 111:187-198.

Brown, D. C. et al, "Ontogeny of T lymphocytes and intestinal morphological characteristics in neonatal pigs at different ages in the postnatal period," J. Anim. Sci. (2006b) 84:567-578.

Casey, P. G. et al, "A five-strain probiotic combination reduces pathogen shedding and alleviates disease signs in pigs challenged with Salmonella enterica serovar Typhimurium," Appl. Environ. Microbiol, (2007) 73:1858-1863.

Cera, K. R. et al, "Effect of age, weaning and post-weaning diet on small intestinal growth and small intestinal morphology in young swine," J. Anim. Sci. (1988) 66:574.

Clean Air "HM Composter and Odor Eliminator," (1 pg).

Coffey, R. et al, "The impact of environment and antimicrobial agents on the growth response of early weaned pigs to spray-dried porcine plasma," J. Anim. Sci. (1995) 73:2532-2539.

Cromwell, G. L. "Antimicrobial and promicrobial agents. In: A. J. Lewis and L. L. Southern (eds.)," Swine Nutrition. p. 611. CRC Press, Boca Raton, FL (2001).

Cruywagen, C. W. et al, "Effect of *Lactobacillus acidophilus* supplementation of milk replacer on preweaning performance of calves," J. Dairy Sci. (1996) 79:483-486.

Davis. M. E. et al, "Effect of direct-fed microbial and antibiotic supplementation on gastrointestinal microflora, mucin histochemical characterization, and immune populations of weanling pigs," Livestock. Sci. (2007) 108:249-253.

Davis, M. E. et al, "Comparison of direct-fed microbial and antibiotic supplementation on innate and adaptive immune characteristics of weaning pigs," Reprod. Nutr. Dev. (2006) 46(Suppl.1):S63.

Davis, M. E. et al, "Rearing environment affects T lymphocyte populations within the systemic circulation and the gastrointestinal tract of young pigs.," Experimental Biology meeting abstracts [on CD Rom]. (2005) The FASEB Journal, 19, Abstract #43.7.

Davis, M. E. et al. "Dietary supplementation with phosphorylated mannans improves growth response and modulates immune function in weanling pigs," J. Anim. Sci. (2004) 82:1882-1891.

Davis, M. E. et al, "Inhalation Toxicology in the Equine Respiratory Tract," In: Equine Respiratory Diseases, P. Lekeux. International Veterinary Information Service (2002).

Donovan, D. C., "Growth and health of Holstein calves fed milk replacers supplemented with antibiotics or enteroguard," J. Dairy Sci. (2002) 85:947-950.

Dritz, S. et al, "Growth and microbial flora of nonmedicated, segregated, early weaned pigs from a commercial swine operation," JAVMA (1996) 208:711.

Dunlop, R. H., "Pathogenesis of ruminant lactic acidosis," Adv. Vet Sci. Comp Med. (1972) 16:259.

Ecological Laboratories, "Microbe-Lift equine products," EQ1, EQ2 and EQ3 (May 2001) (1 pg).

Elam, C. J. "Acidosis in feedlot cattle: Practical observations," J. Anim. Sci. (1976) 43:898.

Fangman, T. et al, "Segregated early weaning," Swine Health Prod. (1997) 5:195.

Fuller, R., "Introduction. In: R. Fuller (Ed.). Probiotics 2: applications and practical aspects," Chapman and Hall, New York (1997) p. 1.

Gaskins, H. R., "Intestinal bacteria and their influence on swine growth In: Austin J. Lewis and Lee L. Southern (Ed.)," Swine Nutrition 2nd Edition. (2001) p. 585-608.

Gebert, S. et al, "Development of a direct fed microbial to control pathogens associated with turkey poult production," Poult. Sci. (2006) 85(suppl. 1):71.

Gebert, S. et al, "Effect of a Bacillus-based direct-fed microbial on turkey poult performance and changes within the gastrointestinal microflora," J. Anim. Sci. (2007) 85(suppl. 1):249.

Hammer, C. et al, "Characterization of a colostrum replacer and a colostrum supplement containing IgG concentrate and growth factors," J. Dairy. Sci. (2004) 87:106-111.

Hatheway, C. L. "Toxigenic Clostridia," Clinical Microbiology Reviews (1990) 3(1):66-98.

Hong, H. A. et al, "The use of bacterial spore formers as probiotics," Fems Microbiol. Rev. (2005) 29:813-835.

Hungate, R. E. et al, "Microbiological and physiological changes associated with acute indigestion in sheep," Cornell Vet. (1952) 42:423.

Janstova, B. et al, "Heat Resistance of Bacillus spp. Spores Isolated form Cow's Milk and Farm Environment," Acta Vet.. Brno (2001) 70:179-184.

Jenny, B. F. et al, "Performance and fecal flora of calves fed a *Bacillus subtilis* concentrate," J. Dairy Sci. (1991) 74:1968-1973.

Jost B. H. et al, "Atypical cpb2 genes, encoding beta2-toxin in Clostridium perfringens isolates of nonporcine origin," Infect. Immun. (2005) 73:652-656.

/K/ "A multiple-strain product containing Bacillus strain BS 27 and strains other than those listed in the pending claims has been sold, at least as early as Jan. 1, 2000.".

King, M. et al, "Terminal restriction fragment length polymorphism analysis of gastrointestinal bacteria from conventional and segregated early weaned pigs: colonization and succession of putative pathogens and potential direct fed microbials," J. Anim Sci. (2005) 83 (Suppl. 1): 197.

Kyriakis, S. C. et al, "The effect of probiotic LSP 122 on the control of post-weaning diarrhea syndrome of piglets," Res. Vet. Sci. (1999) 67:223-228.

La Ragione, R. M. et al, "Competitive exclusion by *Bacillus subtilis* spores of *Salmonella enterica* serotype Enteritidis and Clostridium perfringens in young chickens," Vet. Microbiol, (2003) 94:245-256.

| | State | Reported Genotype | Agtech Multiplex Results |
|---|---|---|---|
| E. 17 Oklahoma | | | K88, LT, STb |
| E. 18 Oklahoma | | | K88, LT, STb |
| E. 25 Iowa | | K88 | K88, STa, STb |
| E. 23 Iowa | | | F18, STx2e, STa, STb |
| E. 20 Iowa | | | F18, STx2e, LT, STb |
| E. 21 Iowa | | F18, STx2e, STb | F18, STx2e, STb |
| E. 24 Iowa | | K88, LT, STa, STb | K88, LT, STa, STb |
| E. 19 Oklahoma | | | K88, STb |
| E. 14 Oklahoma | | | K88, LT, STb |
| E. 16 Oklahoma | | | |
| E. 15 Oklahoma | | | F18, STx2e, STa, STb |
| E. 6 Indiana | | K99 | |
| E. 8 Indiana | | K88 | K88, LT, STb |
| E. 7 Indiana | | K88 | K88 |
| E. 11 Oklahoma | | | K88, LT, STb |
| E. 9 Indiana | | K88 | K88, LT, STb |
| E. 12 Oklahoma | | | K88, LT, STb |
| E. 13 Oklahoma | | | K88, LT, STb |
| E. 10 Indiana | | F41 | |
| E. 1 Indiana | | STx2e | F18, STx2e, STb |
| E. 2 Indiana | | STx2e | F18, STx2e |
| E. 5 Indiana | | F18 | F18 |
| E. 4 Indiana | | F18 | F18 |
| E. 3 Indiana | | F18 | F18 |
| E. 36 Texas | | K99 | STa |
| E. 42 Georgia | | | |
| E. 30 Texas | | K88 | |
| E. 29 Iowa | | K99, STa | STa |
| E. 26 Iowa | | K88 | K88 |
| E. 28 Iowa | | K99, STa | STa |
| E. 31 Texas | | K88 | K88, LT, STb |
| E. 27 Iowa | | K88, STa, STb | K88, STa, STb |
| E. 32 Texas | | K88 | |
| E. 38 Texas | | K88 | K88, LT, STb |
| E. 39 Texas | | K88 | K88, LT, STb |
| E. 45 Georgia | | K88 | K88, LT, STb |
| E. 33 Texas | | K88 | K88, LT, STb |
| E. 34 Texas | | K99 | STa |
| E. 40 Texas | | F18 | F18, STx2e, STa, STb |
| E. 44 Georgia | | K88 | K88, LT |
| E. 43 Georgia | | K88 | K88, LT, STb |
| E. 41 Georgia | | K88 | K88, LT, STb |
| E. 46 Georgia | | K88 | K88, LT, STb |
| E. 50 Georgia | | K88 | K88, LT, STb |
| E. 51 Arkansas | | | F18, STx2e, LT, STa, STb |
| E. 48 Georgia | | K88 | K88, LT, STb |
| E. 47 Georgia | | K88 | K88, LT, STb |
| E. 49 Georgia | | K88 | K88, STa |

FIG. 2

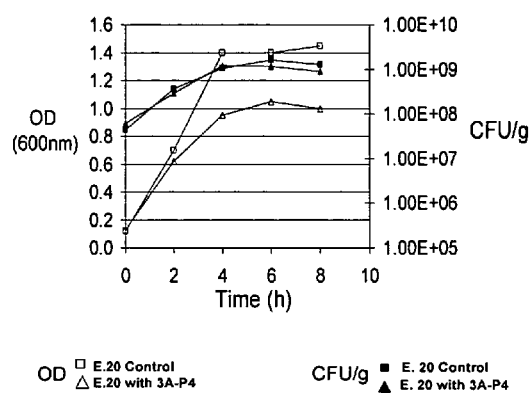
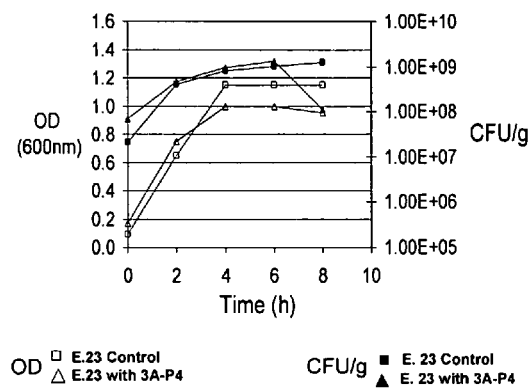
FIG. 12A
FIG. 12B

METHOD AND COMPOSITION FOR REDUCING E. COLI DISEASE AND ENHANCING PERFORMANCE

CROSS-REFERENCE TO RELATED APPLICATIONS

This application claims priority under 35 U.S.C. §119(e) to U.S. Provisional Patent Application No. 60/571,193, filed May 14, 2004, the entirety of which is incorporated by reference herein.

BIBLIOGRAPHY

Complete bibliographic citations of the references referred to herein by a reference numeral in parentheses can be found in the Bibliography section, immediately following the Examples.

FIELD OF THE INVENTION

The invention relates to bacterial strains and the use thereof to control disease in animals and enhance animal performance. More particularly, the invention relates to *Bacillus* strains and their use to control diseases caused by *Escherichia coli* and to enhance animal performance.

BACKGROUND OF THE INVENTION

*E. coli* disease is an important and devastating disease to swine producers. Known for causing edema disease (ED) and post weaning diarrhea (PWD), the economic impact can be substantial with death losses as high as 50% (1). Multiple management and environmental factors have been associated with *E. coli* infections, including age at weaning, diet, crowding, and transportation. Certain host genetic factors, such as having receptors for the *E. coli* fimbriae to attach to the intestinal surface, also contribute to a pig's susceptibility to *E. coli* infection.

ED and PWD are both caused primarily by hemolytic *E. coli* proliferating in the small intestine. *E. coli* infection can also be diagnosed in pigs shortly after birth to two weeks of age (3). ED can occur in pigs between three and eight weeks of age and is characterized by subcutaneous and subserosal edema, a progressive ataxia, paralysis and a high mortality (2). PWD is commonly observed at 7-10 days post weaning but can occur up to eight weeks of age and is characterized by reduced growth rate, severe diarrhea, dehydration, toxemia, or death (2, 3).

Both PWD and ED can occur in the same group of pigs and the causative *E. coli* strains often share certain virulence factors. Usually the first manifestation seen with PWD is sudden death, as early as two days, after weaning. Pigs that do not die suddenly, display a decrease of feed consumption and watery diarrhea which leads to depression and life threatening dehydration. Many pigs show cyanotic discoloration of the tip of the nose, the ears, and the abdomen. Staggering and uncoordinated movements may also be seen in severely affected pigs. Peak mortality generally occurs 6-10 days after weaning. In a herd with PWD, morbidity can vary. Within a litter, the morbidity may be high and reach up to 80% with an average of 30-40%. Mortality in untreated herds can reach 26% (4).

Anorexia is often the first sign seen with edema disease. If diarrhea is to occur, it usually follows after the anorexia. The diarrhea usually disappears by the time the edema and nervous involvement become apparent. Edema can be seen in the eyelids, forehead, ears, and lips. Upon necropsy edema can be seen in the submucosa of the stomach, the mesocolon, gallbladder, and lungs. Progressive ataxia and mental confusion leading to complete recumbence and severe dyspnea are seen in the final stages. The mortality rate in edema disease can reach 50% to over 90% (4).

The source of *E. coli* in a weanling pig is usually derived from the environment either in the nursery, or the pig may acquire the *E. coli* in the farrowing unit and carry it into the nursery. Pathogenic *E. coli* can spread by means of aerosol, feed, farm vehicles, pigs, and other animals (4).

*E. coli* are part of the normal intestinal flora in pigs. Most of the intestinal *E. coli* do not possess the ability to cause disease. These *E. coli* pass through the intestines and are not able to attach to the intestinal wall and do not produce toxins. Those *E. coli* that are pathogenic and cause disease have the ability to do so because they have obtained genes which code for specific virulence factors (5). These virulence factors allow the *E. coli* to adhere to the intestinal wall, colonize the intestine, and produce enterotoxins, which can cause diarrhea and verotoxins which can cause edema disease.

Enterotoxigenic *E. coli* (ETEC) is the major type of *E. coli* implicated in diarrheal disease of pigs (FIG. 1) (5). These strains are characterized by their ability to adhere to the pig intestine and produce enterotoxins. Adherence to the intestinal tract is performed by frimbriae (pili) on the bacteria that attach to receptors located on the intestinal surface. These pili are highly antigenic filamentous protein structures that extend from the surface of the bacteria (5). The major pili found on ETEC are F4 (K88), F5 (K99), F6 (987p), F41, and F18.

Enterohemorrhagic *E. coli* (EHEC) is the major type of *E. coli* implicated in edema disease of pigs. The basis of colonization and toxin production is the same as with the ETEC. The only pilus that has been associated with edema disease in swine is F18, with the F18ab variant being associated more commonly with edema disease. The toxin produced by the EHEC is known as Stx2e. This toxin belongs to a family of toxins called shiga toxins or verotoxins. It is a high molecular weight protein that binds to specific receptors on vascular endothelial cells in certain target tissues (5). Therefore, the disease seen with EHEC is a result of toxemia. The receptor for the toxin is found in blood vessels in the brain, eyelid, stomach wall, mesentery of the colon, and the spinal cord (5). The toxin causes injury and death to the endothelial cells in these target organs.

Enteropathogenic *E. coli* (EPEC) strains, also known as attaching and effacing *E. coli* (AEEC) may play a role in diarrheal disease of pigs. These strains have only recently been investigated as a cause of diarrhea in weaned pigs and were first associated with diarrhea in humans (5). The EPEC cause disease by forming an attachment to the pig intestinal epithelial cells, possibly through the use of pili, and cause destruction of the microvilli (5). The lesions are called attaching and effacing lesions.

No universally effective prophylaxis is available for post weaning *E. coli* disease (4). Fundamental to the prevention of disease is to prevent villous atrophy and colonization (7). Villous atrophy and colonization are related to many factors such as rotavirus infection, diet, STb, and stress (7). Managerial factors that contribute to stress are changes in temperature, overcrowding, feed changes, humidity, and mixing of pigs.

No vaccines are currently commercially available for post weaning *E. coli* disease. However, there are companies that will prepare for each farm a killed or modified live vaccine using one attenuated strain of pathogenic *E. coli* found on the farm. This vaccine generally contains F18 or K88 pili but lacks the toxin genes. The attenuated strain is often grown on the farm and fed or given intranasal to pigs. Toxoids made from Stx2e are also used, but again are not commercially available. These vaccines are often not very pure and even though they may impact mortality due to *E. coli* disease, they generally do not decrease mortality to acceptable levels.

Egg immunoglobin, produced by hens that were vaccinated against fimbrial *E. coli* antigens, have also been developed as an antibody-containing egg powder in pig feed (4). The egg immunoglobin is produced by vaccinating the hen with an attenuated strain of ETEC or with fimbriae from the pathogenic *E. coli* strains. The egg yolks are then collected, and egg yolk antibody powder is then obtained by freeze drying the water soluble protein fraction of egg yolks (9). The theory was that it would provide immune protection against colonization with K88 and F18 positive *E. coli* (4). Marquardt et al. showed that egg-yolk antibodies were able to prevent experimentally induced ETEC diarrhea in 3 day old and 21 day old weaned pigs, and also decreased the occurrence of diarrhea in early-weaned pigs during a field trial study (9). Nevertheless, this is not always what is seen in the field, and producers seem to get mixed results using egg-yolk antibodies. What has been shown is that protection is only provided against challenge strains that have only the F18 fimbriae in common with the vaccine strains (4). Protection may also occur only for the strain of *E. coli* the hen was vaccinated for. Another drawback is that egg immunoglobin can be expensive to include in pig diets.

Some pigs are genetically resistant to ETEC and EHEC strains because they genetically lack the K88 and/or F18 pili receptor. Breeding for genetic resistance can help control *E. coli* disease. The difficult part about this process is the expense of testing and lack of tests available. A proprietary test for the presence of F18 receptors has been developed, but no test exists for the K88 receptor (6).

Antibiotics are often added to feed as a preventative. There are many drawbacks such as consumer acceptance and selection of resistant bacteria (4). Numerous antimicrobial substances are used for this purpose; some include: sulfonamide, trimethoprim, gentamicin, and other aminoglycosides. Isolates from ETEC and EHEC show the highest rate of resistance within swine *E. coli*, and this resistance is often induced within days or a few weeks (4).

Zinc oxide and spray dried porcine plasma included in weanling pig diets have also been used with mixed success.

Once an *E. coli* outbreak occurs, treatment must be administered to decrease mortality and morbidity. Antimicrobial therapy has been the treatment of choice. Antibiotics can be given parenterally or in the water once disease is detected. Antibiotic resistance with *E. coli* isolates is widely known. Pathogenic *E. coli* resistance has been detected against every antibiotic approved for use (4). Electrolytes can also be offered as a treatment choice but can be very costly to the producer.

One important factor that could result in the failure of current treatment and prevention techniques is the high genetic diversity of ETEC and EHEC strains. A high degree of heterogeneity has been shown among isolates from the same state and farm (8). Wilson, et al showed that serotypes associated with post-weaning diarrhea appear to be limited but have very diverse genetic backgrounds (10). This leads one to believe that multiple strains of the same virulence factors or serotype are the cause for a single outbreak of *E. coli* disease on a farm. The cause of heterogeneity is uncertain, but may be due to the fact that gene transfer can readily occur within swine *E. coli*. The fact that antibiotics, vaccines, and other treatments are always being used instigates the need of gene transfer for the survival of pathogenic swine *E. coli*. In addition, the great amount of fecal oral transmission in swine systems provides an environment needed for gene transfer to occur. This heterogeneity is evidence to explain why many traditional methods of treatment and prevention fail.

Therefore, what is needed is one or more isolated *Bacillus* microorganism that is capable of at least one of (A) inhibiting *E. coli* disease and (B) improving performance of an animal. A method of feeding swine one or more of the above-referenced *Bacillus* microorganisms to inhibit *E. coli* disease and/or improve performance of the swine is also needed. Additionally needed is a method of forming a direct-fed microbial from the above-referenced *Bacillus* microorganisms.

SUMMARY OF THE INVENTION

The invention, which is defined by the claims set out at the end of this disclosure, is intended to solve at least some of the problems noted above. Provided is an isolated microorganism of the genus *Bacillus* that is capable of at least one of the following: (A) inhibiting *E. coli* disease and (B) improving performance of an animal. In one embodiment, the microorganism is selected from the group consisting of strains 3A-P4, 15A-P4, and 22C-P1. In another embodiment, the microorganism is strain 15A-P4. A combination of microorganisms comprising at least two of the above-listed microorganisms is also provided.

Additionally provided is a method of feeding swine. In the method, at least one of the above-listed strains is fed to the swine. A method of forming a direct-fed microbial including at least one of the above-listed strains is also provided. In the method at least one of the above-listed strains is grown in a liquid nutrient broth. The microorganism is separated from the liquid to form the direct-fed microbial.

BRIEF DESCRIPTION OF THE DRAWINGS

Preferred exemplary embodiments of the invention are illustrated in the accompanying drawings in which:

FIG. 2 is a dendogram of the *E. coli* isolates obtained from the diagnostic laboratory combining the RAPD analysis using primer 1 and primer 2. Also shown is the multiplex results reported from a diagnostic laboratory and the multiplex results obtained from Agtech Products laboratory.

FIGS. 12A and 12B are the graphs showing the mode of action of the active metabolite produced by 3A-P4 on *E. coli* strain E.20 (FIG. 12A) and *E. coli* strain E.23 (FIG. 12B).

Figure 1:
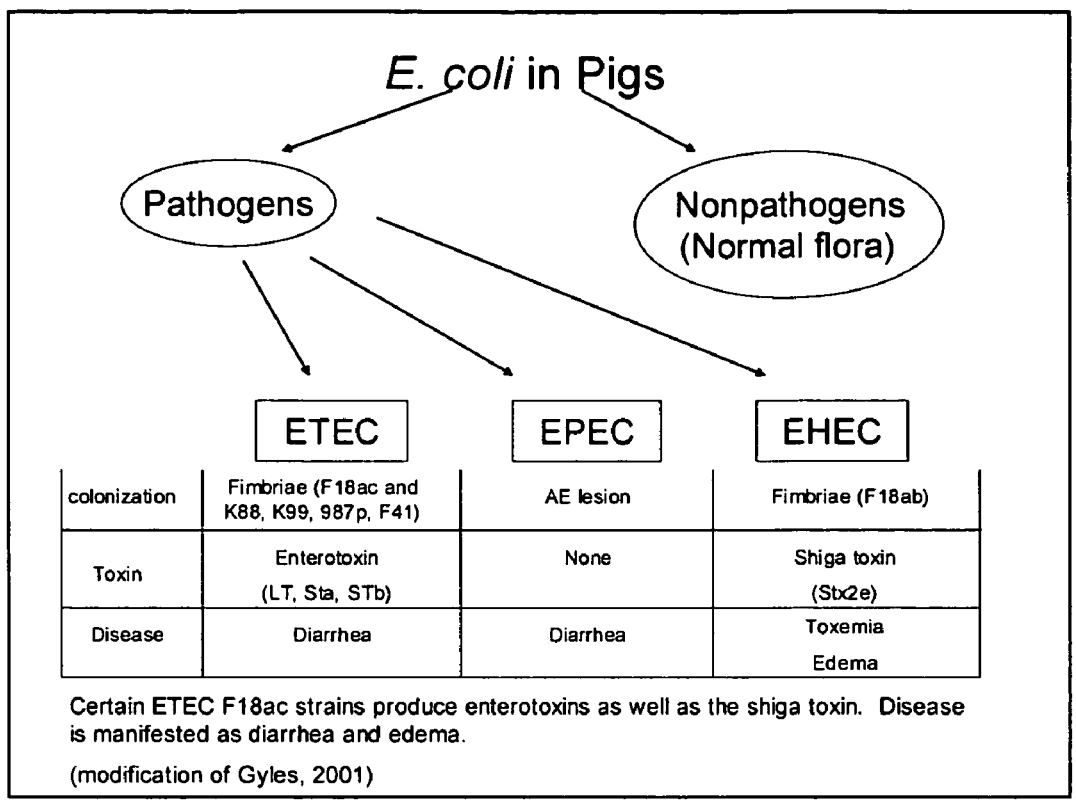
FIG. 1 is a diagram showing colonization and disease due to Enterotoxigenic *E. coli* (ETEC), Enteropathogenic *E. coli* (EPEC), and Enterohemorrhagic *E. coli* (EHEC).

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting. The references cited throughout the application are incorporated by reference herein.

DETAILED DESCRIPTION

Definitions

The following definitions are intended to assist in providing a clear and consistent understanding of the scope and detail of the terms:

As used herein, "active metabolite" means a substance produced by bacteria and which has antibacterial activity towards other genuses of bacteria.

As used herein, "animal" means a multicellular organism of the kingdom Animalia.

As used herein, "bacteriocin" means a substance produced by bacteria and which has antibacterial activity towards other genuses of bacteria.

As used herein "basemix" or "concentrated basemix" refers to *Bacillus* strains added to a carrier to make a basemix form. The concentrated form is composed of the *Bacillus* strains added the carrier in a more concentrated form. The basemix or concentrated basemix forms are then be added to the feed at a desired inclusion rate and fed to the animal.

As used herein, "performance" refers to the growth of an animal, such as a pig, measured by the following parameters: average daily gain (ADG), weight, mortality, feed conversion, which includes both feed:gain and gain:feed, and feed intake.

"An improvement in performance" as used herein, means an improvement in at least one of the parameters listed above under the performance definition.

In accordance with the present invention there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

Aerobic and facultative sporeformers of the genus *Bacillus* were isolated. *Bacillus* species are the only sporeformers that are considered GRAS, i.e., generally recognized as safe. In a preferred embodiment, a *Bacillus* species was included only if it had GRAS status. The *Bacillus* species were isolated from environmental samples such as poultry litter and animal waste and screened. Other sources of *Bacillus* can also be screened. The *Bacillus* strains were screened for their ability to inhibit growth of pathogenic swine *E. coli*. Although not intended to be a limitation to the present disclosure, it is believed that inhibition is accomplished via the secretion of an active metabolite from the *Bacillus*. While applicants do not wish to be restricted to a particular theory of how the active metabolite inhibits microbial growth and do not intend to limit the present disclosure, it is believed that the active metabolite is a proteinaceous substance and, more specifically, it is believed to be a bactericidal.

The *Bacillus* isolates were tested for their ability to inhibit various pathogenic strains of swine *E. coli*. The *E. coli* strains were obtained from animal diagnostic laboratories, swine environment, and fecal matter. The *E. coli* strains were shown to be pathogenic by performing multiplex PCR to detect pili and toxin genes associated with pathogenic *E. coli* disease in swine. To test for production of active metabolite, *Bacillus* isolates were replica plated onto pathogen indicator plates, which were formed from a 1% pathogen inoculum of a pathogenic swine *E. coli* strain.

Additionally, the active metabolite activity of the *Bacillus* isolates was reconfirmed using a spot assay method. The *Bacillus* isolates were then tested using appropriate biochemical tests to determine whether the isolates had GRAS status.

The spectrum of activity of the various *Bacillus* isolates was then determined. The *Bacillus* isolates were tested for activity against the known swine *E. coli* pathogens collected from different regions of the United States using the spot assay method. This was done to confirm that the activity produced by the *Bacillus* isolates would be useful throughout the United States. The *Bacillus* isolates that showed the highest inhibitory activity against numerous pathogenic *E. coli* strains were further characterized for their activity level.

From these experiments, three preferred *Bacillus* strains were found: 3A-P4, 15A-P4, and 22C-P1, although other strains can also be used. These strains were preferred because of the number of pathogenic *E. coli* strains that each inhibited and because of their GRAS status. On Jan. 12, 2005, strains 3A-P4, 15A-P4, and 22C-P1 were deposited at the American Type Culture Collection, 10801 University Blvd., Manassas, Va. 20110-2209 and given accession numbers PTA-6506 (3A-P4), PTA-6507 (15A-P4), and PTA-6508 (22C-P1). The deposits were made under the provisions of the Budapest Treaty on the International Recognition of the Deposit of Microorganisms for the Purposes of Patent Procedure.

Strains 3A-P4, 15A-P4, and 22C-P1, can be fed individually or in combination, to swine, although other strains are included within the scope of the invention. For the *Bacillus* strains 3A-P4, 15A-P4, and 22C-P1, growth times were determined for production of an optimal level of the active metabolite using the broth activity method. The assay incubation time at which optimal inhibition of *E. coli* occurred was also determined using the broth activity method. For this, active metabolite was added to a culture of *E. coli* and ODs were read at various time points. The *Bacillus* isolates 3A-P4, 15A-P4, and 22C-P1 were tested for activity against 142 known swine *E. coli* pathogens collected from different regions of the United States using the broth activity method. These strains inhibited to varying degrees one hundred percent of the *E. coli* strains tested. The strains can be used alone or in combination to inhibit growth of pathogenic swine *E. coli*.

The three preferred *Bacillus* isolates of the invention were isolated from different geographical regions of North America and from different environmental sources. Specifically, strain 3A-P4 was isolated from chicken litter from Canada, strain 15A-P4 was isolated from turkey litter from the Western United States, and strain 22C-P1 was isolated from a swine lagoon from the Eastern United States.

The active metabolite was then purified from each of the *Bacillus* isolates to two levels: first, a crude purification of the active metabolite was obtained by filtering the culture supernatant, and second, a partially purified active metabolite was obtained by salting out the active metabolite and then fractionating it by column chromatography. The stability and characterization of the active metabolite was then determined using the crude form of the active metabolite by performing enzyme and heat degradation assays, mode of action assays, and antibiotic sensitivity assays. Optimal media and time conditions were also determined for cell growth and spore formation.

Further characterization of the *Bacillus* isolates 3A-P4, 15A-P4, and 22C-P1 was performed, including DNA fingerprinting and determining stability of the isolates in a swine premix at 60° C. for 8 weeks.

Through field trial studies, it was determined that the *Bacillus* strains also enhance nursery swine performance. Therefore, it is economical for a producer to routinely include the *Bacillus* strains, either individually or in combination, in feed not only to prevent *E. coli* disease but also to enhance performance.

The *Bacillus* isolates of the invention, which inhibit pathogenic *E. coli*, can be directly fed to swine to inhibit pathogenic swine *E. coli* disease and to enhance swine performance. Feeding microorganisms that have GRAS status to livestock is an acceptable practice amongst producers, veterinarians, and others in the livestock industry. By inhibiting this pathogen in the swine, the *Bacillus* isolates reduces and even prevents *E. coli* disease in swine.

The *Bacillus* isolates can be administered as a preventative to swineherds not currently infected with pathogenic *E. coli*. In a preferred embodiment, newly weaned pigs are fed the *Bacillus* isolates throughout the nursery phase to inhibit or even prevent outbreaks of *E. coli* disease and to enhance performance. However, one or more *Bacillus* isolate can be fed at other phases also. Routine administration of the microorganisms dramatically reduces and even eliminates outbreaks of *E. coli* disease at animal production facilities and enhances swine performance.

The *Bacillus* isolates can be administered as a direct-fed microbial. Administration of one or more direct-fed microorganisms to animals is accomplished by any convenient method, including adding the *Bacillus* isolates to the animals' drinking water or to their feed, or by direct oral insertion. In a preferred embodiment, the microorganism is fed to animals by adding it to the animals' feed or water. *Bacillus* isolates preferably are administered as spores.

The *Bacillus* isolates may be presented in various physical forms, for example as a top dress, liquid drench, gelatin capsule, gel, or added to the water. In feed form, the isolates may be presented in a form as a basemix or a concentrated form of the basemix. In a preferred embodiment of a top dress form, freeze-dried *Bacillus* fermentation product is added to a carrier, such as whey, maltodextrin, sucrose, dextrose, limestone ($CaCO_3$), rice hulls, yeast culture, dried starch, or sodium silico aluminate.

In a preferred embodiment of the liquid drench form, freeze-dried *Bacillus* fermentation product is added to a carrier, such as whey, maltodextrin, sucrose, dextrose, dried starch, or sodium silico aluminate, and a liquid is added to form the drench.

In a preferred embodiment of the gelatin capsule form, freeze-dried *Bacillus* fermentation product is added to a carrier, such as whey, maltodextrin, sugar, limestone ($CaCO_3$), rice hulls, yeast culture dried starch, or sodium silico aluminate. The *Bacillus* isolates and carrier can be enclosed in a gastrointestinal-degradable gelatin capsule.

In a preferred embodiment of the gel form, freeze-dried *Bacillus* fermentation product is added to a carrier, such as vegetable oil, sucrose, silicon dioxide, polysorbate 80, propylene glycol, butylated hydroxyanisole, and citric acid, or artificial coloring to form the gel. In a preferred embodiment of the water form, the freeze-dried *Bacillus* fermentation product is added to a carrier, such as sucrose, dextrose, sodium silico aluminate, and artificial coloring.

In a preferred embodiment of the basemix or concentrated basemix form, the freeze-dried *Bacillus* fermentation product is added to a carrier, such as, but not limited to, rice hulls, dried brewers grain, limestone, or baylith for moisture control. Other carrier that are suitable and compatible for these strains can also be used.

The microorganisms can be administered as spray-dried, freeze-dried, fluidized bed dried, used in a solid state fermentation form, as well as other forms. For freeze drying, the wet cell paste preferably is then mixed with cryoprotectants, which maintain the viability of the cells during the freezing and drying process. The mixture is then placed in trays, frozen and subsequently dried. For spray drying, the paste or slurry is then mixed with spray drying aids, if applicable, and spray dried. The resulting dried cake, obtained from drying methods or solid state fermentation method, is then milled to a uniform size and plated to determine the activity. After a viable cell count has been determined, the cell count preferably is standardized to a predetermined activity level or colony forming units (CFU) per gram by blending with dry carriers.

To produce the *Bacillus* isolates, one or more isolates are grown in a liquid nutrient broth, such as TSB, preferably to a level at which the highest number of spores are formed. In a preferred embodiment, the isolates are grown to an OD where the spore yield is at least $1 \times 10^9$ colony forming units (CFU) per ml of culture. The bacterial strains of the present invention are produced by fermentation of the bacterial strains. fermentation is started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation. The count of the culture can then be determined.

The count of the bacteria is important when combined with a carrier. At the time of manufacture of the composition, the *Bacillus* count preferably is at least about $1.0 \times 10^{11}$ CFU/g. The counts may be increased or decreased from these base numbers and still have complete efficacy. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

To prepare the compositions, the cultures and the carrier can be added to a ribbon or paddle mixer and mixed preferably for about 15 minutes. The components are blended such that a uniform mixture of the carrier and cultures result. The final product is preferably a dry flowable powder. Exemplary carriers in this composition are rice hulls, dried brewers grain, limestone, baylith, or other suitable carriers for microorganisms.

The preferred dosage range of the liquid drench, gelatin capsule, and gel is about $1 \times 10^4$ CFU/g or ml/day to about $1 \times 10^{10}$ CFU/g or ml/day, and more preferably about $1 \times 10^6$ CFU/g or ml/day. The preferred dosage range of the top dress, basemix, and premix is about $1 \times 10^3$ CFU/g of feed to about $1 \times 10^8$ CFU/g of feed, and more preferably about $1 \times 10^6$ CFU/g of feed. The preferred dosage range for inclusion into water is about $1 \times 10^3$ CFU/pig/day to about $1 \times 10^{10}$ CFU/pig/day, and more preferably about $1 \times 10^8$ CFU/pig/day. While these examples use freeze-dried *Bacillus* as an ingredient in the top dress, liquid drench, gelatin capsule, gels, water, and feed forms it is not necessary to freeze-dry the *Bacillus* before feeding it to swine. For example, spray-dried, fluidized bed dried, or solid state fermentation *Bacillus* or *Bacillus* in other states may be used. The microorganisms can also be administered in a wet cell slurry paste, with or without preservatives, in concentrated, unconcentrated, or diluted form.

The composition used in the Examples below was produced as follows: strain 3A-P4 with a count of $7 \times 10^{11}$ CFU/g, 15A-P4 with a count of $8.4 \times 10^{11}$ CFU/g, and 22C-P1 with a count of $6 \times 10^{11}$ CFU/g were combined in different ratios with carriers to determine the best ratio to inhibit pathogenic swine *E. coli* and enhance nursery performance. The combinations were as follows: Product 1: 30% of the total count of strain 3A-P4, 60% of the total count of strain 15A-P4, 10% of the total count of strain 22C-P1 for a final bacteria count of $5.1 \times 10^8$ CFU/g; Product 2: 100% of the total count of strain 22C-P1 with a final bacteria count of $4.5 \times 10^8$ CFU/g; and Product 3: 90% of the total count of strain 22C-P1, 10% of the total count of strain 15A-P4 with a final bacteria count of $5.1 \times 10^8$ CFU/g. In the Examples, all the above combinations were added to the feed for a final count of $1 \times 10^6$ CFU/g of feed and were fed throughout the nursery phase. Carriers used in all combinations used in the experiments were 40% rice hulls, 19% dried brewers grain, 40% limestone, and 1% baylith for moisture control. A preferred combination is 90% of the total count of strain 22C-P1 and 10% of the total count of strain 15A-P4. This combination was found to be effective in decreasing swine *E. coli* disease and enhancing swine performance.

Additional combinations and single-strain compositions that are useful include an about 90% of the total count of strain 15A-P4 and about 10% of the total count of strain 22C-P1 combination with a final bacteria count of about $1 \times 10^6$ CFU/g of feed and 100% 15A-P4 with a final bacteria count of about $1 \times 10^6$ CFU/g of feed.

*Bacillus* strains provided herein are capable of at least one of the following in swine: (A) inhibiting *E. Coli* disease and B) improving performance. One or more of the *Bacillus* strains have been shown to be effective for these purposes when fed to nursery pigs. It is believed that feeding one or more *Bacillus* strain provided herein would also be useful when fed to pigs at other stages in their lives. For instance, it is believed that feeding one or more *Bacillus* strain to breeding stock, including sows, gilts, and boars, and to lactation-phase piglets, and finishing pigs would also provide benefits of inhibiting *E. coli* disease and/or improving performance.

One or more of the *Bacillus* strains has also been shown to be beneficial when fed to poultry. For example, populations of avian pathogenic *E. coli* have been reduced when strain 15-A-P4 was fed to poultry.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Isolation of Active Metabolite Producing *Bacillus* Strains and Isolation of Pathogenic Strains A. *Bacillus* Strains and Media Microbial strains from chicken litter, turkey litter, swine waste, and dairy waste, were screened for *Bacillus* strains. The environmental sample was weighed and mixed with sterile peptone blanks to make a $10^{-1}$ dilution. To pasteurize and, thus, to select for aerobic and facultative sporeformers, the sample was placed in a masticator for one minute and then heated for thirty minutes in a 63° C. water bath. The sample was then serially plated onto Tryptic Soy Agar (TSA) and incubated at 32 degrees for 24-48 hours to obtain isolates.

B. Pathogen *E. coli* Strains and Media

An initial collection of pathogen strains was obtained from a swine diagnostic laboratory. This included two K88 and one F18 *E. coli* strains. The isolates were stored as frozen stocks at −85° C. in TSB supplemented with 10% glycerol. For the initial screening process, the three *E. coli* strains were utilized in assays to screen *Bacillus* isolates for activity against *E. coli*. Swine *E. coli* pathogens tested were grown overnight in tryptic soy broth (TSB) at 37° C. A one percent inoculum was transferred into its corresponding media the next day and incubated at 37° C. until OD value at 600 nm was at 0.600.

Example 2

Activity of *Bacillus* Isolates Against *E. coli*

A. Zone of Inhibition Assay

Activity against *E. coli* was determined by replica plating the *Bacillus* isolates onto indicator plates containing swine *E. coli* pathogens. Pathogen indicator plates were formed by transferring one percent of one of the swine *E. coli* pathogen inoculum, grown as described above, into tempered TSA. Seven milliliters of this agar was poured into a petri dish to make the pathogen indicator plates. The *Bacillus* isolates were replica plated onto pathogen indicator plates and were incubated overnight at 32° C. Plates were then observed for zones of inhibition for each pathogen. The *Bacillus* isolates that produced zones of inhibition were picked off the plate and grown in TSB to isolate the colony for reconfirmation of its activity. The isolates were stored as frozen stocks at −85° C. in TSB supplemented with 10% glycerol. Thirty thousand *Bacillus* isolates were screened for activity against *E. coli*. Fifty isolates produced activity against *E. coli*.

B. Spot Assay

Activity of the 50 *Bacillus* isolates was confirmed using the spot plate assay method by growing the isolates in TSB overnight at 32° C. Ten microliters of the *Bacillus* isolate was then spot plated onto pathogen indicator plates made as described above. Indicator plates were incubated 24 hours at 32° C. and were observed for zones. Thirty six of the fifty isolates displayed activity against *E. coli* upon reconfirmation using the spot assay method. Table 2 shows the *Bacillus* strains that had activity against one or more of the *E. coli* strains. It should be noted that some *Bacillus* strains had activity against more than one *E. coli* strains.

TABLE 2

Summary of Active Metabolite Producing *Bacillus* Isolates Against *E. coli*.

| INDICATOR STRAIN | POSITIVE *BACILLUS* STRAINS |
| --- | --- |
| *Escherichia coli* K88 strain BH | 15 |
| *Escherichia coli* K88 strain S | 9 |
| *Escherichia coli* F18 strain 8A133 | 16 |

Example 3

Biochemical Tests on *Bacillus* Isolates

All *Bacillus* isolates that were confirmed to produce active metabolites were biochemical tested to identify isolates that were generally recognized as safe (GRAS). Testing was performed by both (1) traditional lab methods, including Gram stain, colony morphology, catalase production, starch utilization, casein utilization, nitrate reduction, indole formation, Voges-Proskauer, gelatin hydrolysis, and citrate production and (2) an API *Bacillus* biochemical test kit available from bioMérieux of Hazelwood, Mo. Thirty-six *Bacillus* isolates were screened using traditional biochemical methods, which showed that six of the thirty-six isolates tested as possible GRAS strains. These isolates were retested using the API test kit, and results showed that all six isolates were confirmed as belonging to species that are GRAS. The isolates producing the widest spectrum of activity against *E. coli* were biochemical tested using an outside reference laboratory for final identification.

Example 4

Determination of Spectrum of Activity Against *E. coli* of *Bacillus* Isolates

A. Spot Plate Procedure to Determine Spectrum of Activity Against *E. coli*

To confirm that the six GRAS *Bacillus* isolates were also effective against *E. coli* pathogens from other regions of the United States, a broad collection of porcine *E. coli* pathogens were selected from various animal diagnostic laboratories from Indiana, Oklahoma, Iowa, and Texas. Nineteen other GRAS *Bacillus* isolates that demonstrated against other pathogens were also screened against diagnostic laboratory *E. coli* pathogens. Some of these additional strains are included Table 4 below.

Upon arrival, pathogens were immediately grown in either TSB overnight at 37° C. Streak plates of each culture were made to ensure pure colonies, which were grown again in their respective media overnight at 37° C.

Forty porcine *E. coli* isolates were obtained. *E. coli* strains represented were K88, K99, 987p, F18, F41, and 718. Toxins produced by the *E. coli* included the enterotoxins LT (heat-labile enterotoxin), Sta (heat-stable enterotoxin a), and STb (heat-stable enterotoxin b); and the Shiga-like toxin Stx2e (subgroup Stx2 with variant form e). Thirty-seven of the forty *E. coli* isolates were confirmed as *E. coli* using an API biochemical test kit.

The twenty-five GRAS *Bacillus* isolates, which included the six isolates that showed activity against the original three *E. coli* isolates and the nineteen isolates that showed activity against other pathogens, were tested for activity against the thirty-eight *E. coli* porcine pathogens, using the spot assay method described above in Example 2B. For each *Bacillus* isolate, an individual colony was grown overnight in TSB at 32° C. and was used as the antimicrobial producer culture.

Pathogen indicators were prepared as follows: *E. coli* was grown in TSB for 24 hours at 37° C. After 24-48 hours of growth, the pathogen indicators were transferred at 1% into new media and incubated at 37° C. until an OD of 0.6-1.0 at 600 nm was achieved. The pathogen indicator plates were prepared as described above. Five microliters of the *Bacillus* culture was spot plated onto the indicator plate and incubated for 24 hours at 32° C. Then, plates were observed for zones of inhibition.

As shown in Table 3 18 of the 25 *Bacillus* strains displayed inhibitory activity against the thirty-seven *E. coli* isolates, indicating that an active metabolite that inhibited the pathogen was being produced. Strain 3A-P4 inhibited eleven *E. coli* isolates, 15A-P4 inhibited fourteen *E. coli* isolates, and 22C-P1 inhibited eighteen *E. coli* isolates. Strains 3A-P4, 15A-P4, and 22C-P1 were chosen for further characterization due to their increased activity against *E. coli* compared to the other 25 GRAS isolates. The three strains 3A-P4, 15A-P4, and 22C-P1 were tested against >140 pathogenic swine *E. coli* isolates. Each of the three *Bacillus* strains inhibited the >140 *E. coli* isolates by differing percentages.

TABLE 3

Number of *E. coli* Strains Inhibited by *Bacillus* Isolates.

| *Bacillus* Isolate | *E. coli* |
|---|---|
| 3A-P4 | 11 |
| 3B-P5 | 2 |
| 3C-P2 | 5 |
| 6A-P1 | 1 |
| 6A-P2 | 2 |
| 6A-P5 | 0 |
| 6A-P6 | 1 |
| 6A-P8 | 1 |
| 6A-P12 | 1 |
| 7E-P1 | 0 |
| 9A-P1 | 0 |
| 10A-P4 | 4 |
| 10A-P5 | 0 |
| 10A-P6 | 2 |
| 10B-P1 | 2 |
| 10D-P1 | 3 |
| 10F-P3 | 1 |
| 10F-P5 | 2 |
| 10I-P1 | 4 |
| 10K-P1 | 2 |
| 14C-P1 | 0 |
| 14D-P1 | 0 |
| 15A-P4 | 14 |
| 15B-P3 | 0 |
| 22C-P1 | 18 |

B. Characterization of the *E. coli* Isolates

Multiplex, RAPD, and pulse-field gel electrophoresis was performed on the *E. coli* isolates obtained from diagnostic laboratories. Upon arrival the isolates were grown and stored as previously described.

All the *E. coli* isolates were genotyped by Agtech Products using multiplex PCR. This procedure distinguished *E. coli* that contained virulence factors responsible for causing disease in swine. Purified genomic DNA was isolated using a DNA isolation kit (Roche, Indianapolis, Ind.). The multiplex procedure was performed using the Amplitaq Gold DNA polymerase reagents (Roche, Branchburg, N.J.) (7). Nine oligionucleatide primers were used in the multiplex procedure to detect the STX2e, LT, STa, and STb toxins; and the K88, K99, F18, 987p, and F41 pili. DNA fragments were separated using a 3.0% Nusieve 3:1 agarose gel (Biowhittaker, Rockland, Me.).

The pathogenic *E. coli* isolates were genetically analyzed using the RAPD method. *E. coli* isolates were grown in TSB overnight until an OD of 4.0 at 600 nm was obtained. Purified genomic DNA was isolated using Roche Molecular Biochemicals DNA isolation kit (Indianapolis, Ind.). Once the DNA was isolated, RAPD analysis was performed using Ready-To-Go RAPD Analysis Bead kit from Amersham Pharmacia Biotech (Piscataway, N.J.). RAPD analysis was performed using two 10-base pair oligionucleatide primers in a polymerase chain reaction. The DNA fragments were separated using a 1.5% agarose gel in 0.5× TBE buffer at 100 volts.

Pulsed-field gel electrophoresis (PFGE) was performed using chromosomal DNA embedded in agarose beads and digested with Xba I via a modification of the method of Rehberger (12). DNA fragments were separated on 0.8% agarose gel using a CHEF-DR III electrophoresis system (Bio-Rad).

DNA bands were visualized following ethidium bromide staining and digitally captured using Syngene Genesnap darkroom software (Frederick, Md.). The determination of the molecular size of the DNA fragments and dendogram were accomplished using Bionumerics software (Kortrigjk, Belgium).

The population of *E. coli* isolated from infected swine herds was heterogeneous, as is shown in the Dendogram of FIG. 2. RAPD analysis differentiated the 48 isolates into 48 genotypic patterns. Of the 48 genotypes, 12 clusters containing 2 or more isolates were identified at a coefficient of similarity of 65% or greater. The largest cluster contained 7 isolates. Eight isolates had less than 67% similarity to any other isolate.

PFGE of intact chromosomal DNA digested with Xba 1 differentiated 42 isolates into 42 genotypic patterns. Six of the 48 isolates did not produce discernible fragments using PFGE. Of the 42 RAPD patterns, 3 clusters containing 2 or more isolates were identified at a coefficient of similarity of 67% or greater. The largest cluster contained 5 isolates. Thirty-six isolates had less than 67% similarity to any other isolate.

Example 5

Characterization of *Bacillus* Strains 3A-P4, 15A-P4, and 22C-P1

A. DNA Fingerprinting

Figure 3:
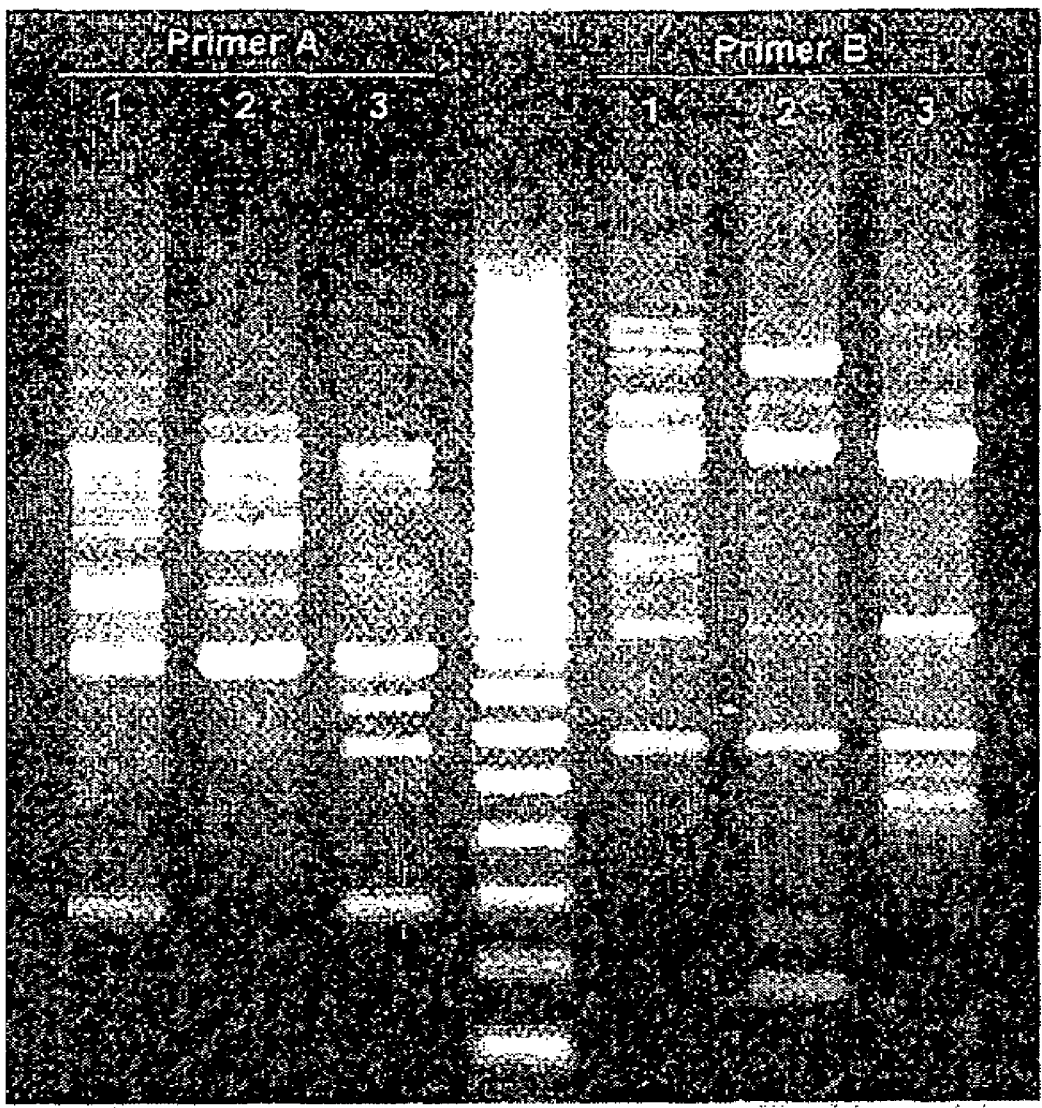
FIG. 3 is a gel image of two sets of DNA fingerprints for three preferred strains of *Bacillus* isolates: 3A-P4 (lanes 1 and 5), 15A-P4 (lanes 2 and 6), and 22C-P1 (lanes3 and 7). A 100 bp molecular weight marker (Bio-Rad, Hercules, Calif.) is in lane 4. Two different 10 bp primers were used for two sets of random amplified polymorphic DNA analysis on the isolates, with results of the first set shown in lanes 1-3, and results of the second set shown in lanes 5-7.

DNA fingerprinting of strains 3A-P4, 15A-P4, and 22C-P1 was performed by random amplified polymorphic DNA (RAPD) PCR analysis on genomic DNA isolated from strains 3A-P4, 15A-P4, and 22C-P1 using Roche Molecular Biochemicals DNA isolation kit (Hoffmann-La Roche, Inc., Nutley, N.J.). RAPD PCR analysis was performed using Ready-to-go RAPD Analysis Bead kit from Amersham Pharmacia Biotech (Piscataway, N.J.) using two different 10-base pair oligonucleotide primers in two sets of polymerase chain reactions. The two sets of DNA banding patterns, generated from two different 10 bp primers, from the 3A-P4, 15A-P4, and 22C-P1 strains are shown in FIG. 3 with a Bio-Rad 100 bp molecular weight marker, in lane 4, separating the sets. Although some bands were shared between the strains, no common DNA fingerprint was found between the three strains, which indicates that 3A-P4, 15A-P4, and 22C-P1 are different strains.

B. Stability in Premix

Strains 3A-P4, 15A-P4, and 22C-P1 were added at $5.0 \times 10^8$ to 500 g of swine ration premix. Premix was incubated in a 60° C. drying oven for eight weeks. Spore enumeration was performed weekly at $10^{-6}$, $10^{-7}$, and $10^{-8}$.

No decrease in spore count was evident during this assay. Strains 3A-P4, 15A-P4, and 22C-P1 were viable in premix rations containing primarily minerals at temperatures that may be found in warmer climates when feed is stored in warehouses, barns, or feed bins. This assay also displayed that these *Bacillus* strains are viable at a high mineral concentration.

C. Antibiotic Sensitivity

Strains 3A-P4, 15A-P4, and 22C-P1 were grown in 50 ml of TSB overnight at 32° C. with shaking. 1.0% of each strain was inoculated individually into TSA and poured into petri dishes. After the plates were solidified, the antibiotic discs were placed onto the agar surface. The plates were incubated at 32° C. overnight. Inhibitory zones were measured in millimeters.

The antibiotics caused minimal sized zones of inhibition against the three *Bacillus* strains (Table 4). Therefore, the antibiotics should not interfere with the growth of 3A-P4, 15A-P4, and 22C-P 1.

Further testing by broth and agar assays was performed with the antibiotic ASP-250 (chlortetracycline, sulfathiazole, and penicillin combined) against 3A-P4, 15A-P4, and 22C-P1. This antibiotic decreased the growth of 3A-P4, 15A-P4, and 22C-P1 by 99.9%. This antibiotic is bactericidal to the *Bacillus* strains.

TABLE 4

Antibiotic Sensitivity Assay of Strain 3A-P4, 15A-P4, and 22C-P1.

| Antibiotic Disc | Inhibitory Zones Measured in Millimeters | | |
|---|---|---|---|
| | 3A-P4 | 15A-P4 | 22C-P1 |
| Oxytetracycxyline 30 µg | 24 | 14 | 24 |
| Tetracycline 5 µg | 26 | 14 | 21 |
| Gentamycin 10 µg | 26 | 22 | 22 |
| Neomycin 5 µg | 16 | 12 | 12 |
| Penicillin 2 IU | 0 | 11 | 13 |
| Bacitracin 10 IU | 8 | 8 | 8 |
| Lincomycin 2 µg | 8 | 9 | 8 |

Example 6

Biochemical Testing of the Three *Bacillus* Isolates, 3A-P4, 15A-P4, and 22C-P1

Strains 3A-P4, 15A-P4, and 22C-P1 were further biochemical tested using MIDI laboratory. Ribosomal DNA analysis using Genbank showed that these strains were *Bacillus subtilis* strains. *Bacillus subtilis* is a species of *Bacillus* that is considered GRAS.

Example 7

Purification of Active Metabolite from *Bacillus* Isolates and Characterization of Activity Against *E. coli*

A. Crude Purification of Active Metabolite

To further optimize the *Bacillus* strains for optimal active metabolite production and to further characterize the active metabolite for identification a new assay was introduced. This assay, called the broth activity assay, involved using the active metabolite in a crude form so further characterization and optimization tests could be performed without interference from the *Bacillus* cells. This assay also allows a more quantified result that is reported as percent inhibition. An individual colony of each *Bacillus* isolate was picked and inoculated into 50 mls of TSB and incubated at 32° C. with shaking overnight. After 18 hours of incubation, 10 mls of the producer strain was harvested by centrifugation at 5000 rpm for 10 minutes, and the supernatant was filtered through a 0.2 um acrodisc filter. The filtered supernatant, the crude purified form of the active metabolite, was utilized immediately or stored frozen for no longer than two days before being used in an assay. From an isolated colony, *E. coli* pathogens were grown in TSB at 37° C., with at least two 1% transfers until an OD of 0.6 at 600 nm was reached. A test tube with TSB was inoculated with the crude form of the active metabolite and the *E. coli* inoculum. A separate test tube with TSB was inoculated with only the *E. coli* inoculum and incubated at 37° C. Percent inhibition was determined as follows: (0% OD−sample OD)/0% OD*100. To perform this assay correctly, the amount of the crude form of active metabolite needed in the assay, optimal growth time, and OD for the *Bacillus* isolates to produce an optimal active metabolite level, and the incubation time of the assay was determined.

B. Active Metabolite Percentage Needed for the Broth Activity Assay

Trials were performed to determine the optimal percentage of active metabolite needed to inhibit *E. coli* in the broth assay. *Bacillus* isolates 3A-P4, 15A-P4, and 22C-P1 were tested against the swine pathogenic *E. coli* strains. *E. coli* isolates E.20 and E.23 were chosen to be used as screening pathogens because all three preferred *Bacillus* isolates (3A-P4, 15A-P4, and 22C-P1) had shown inhibitory activity against these pathogens. From an isolated colony, pathogens were grown in TSB at 37° C., with at least two 1% transfers until an OD of 0.6 at 600 nm was reached. TSB tubes were inoculated at 1% with the pathogen and 10%, 5%, 1%, 0.5%, and 0% with the crude purified form of the active metabolite, collected as previously described, and incubated at 37° C. An OD was read at 4 and 8 hours to determine percent inhibition at each active metabolite percent level. Percent inhibition was determined as follows: (0% OD−sample OD)/0% OD*100. Results are shown in Table 5. The active metabolite added at 10% showed the greatest inhibition of *E. coli*. Inhibition was also observed at the other levels. From these results, it was determined the active metabolite added at 10% would yield enough inhibition to be detected with further characterization and optimization tests. Therefore, this percent was used in subsequent studies.

TABLE 5

Inhibition of *E. coli* in Broth Using Different Percentages of Active Metabolite

| *Bacillus* Isolate | Inoculated Metabolite Percentage | Percent Inhibition *E. coil* E. 20 | | Percent Inhibition *E. coli* E. 23 | |
|---|---|---|---|---|---|
| | | 4 h | 8 h | 4 h | 8 h |
| 3A-P4 | 10 | 18.8 | 26.7 | 32.6 | 20.8 |
| | 5 | 9.0 | 13.3 | 5.3 | 8.3 |
| | 1 | 0 | 6.7 | 5.3 | 0 |
| | 0.5 | 0 | 6.7 | 0 | 0 |
| 15A-P4 | 10 | 13.6 | 7.1 | 15 | 0 |
| | 5 | 9.1 | 0 | 10 | 0 |
| | 1 | 0 | 0 | 5 | 0 |
| | 0.5 | 0 | 0 | 5 | 0 |
| 22C-P1 | 10 | 13.6 | 7.4 | 15.8 | 4.3 |
| | 5 | 9.1 | 3.7 | 5.3 | 4.3 |
| | 1 | 0 | 0 | 5.3 | 0 |

C. Active Metabolite Production Time

Incubation time trials were performed to determine the optimal growth time and OD for the *Bacillus* isolates to produce an optimal active metabolite level. Percent inhibition against *E. coli* strain E.20 was performed and used as the indicator strain. Strains 3A-P4, 15A-P4, and 22C-P1 were used.

Growth times and ODs under which the *Bacillus* isolates were found to produce the most active metabolite and therefore display the greatest amount of inhibition against E. 20 were determined by sampling the culture at 12-hour intervals. At the time points, the crude purified form of the active metabolite was obtained as previously described and inoculated at 10% into 10 ml of TSB. Strain E. 20 was used as the indicator organism and grown as described previously. Strain E.20 was added at 1% to the TSB tubes containing the active metabolite. The assay was incubated at 37° C. and OD read at 5 h and 10 h. A control tube with the indicator organism, added at 1% to a 10 ml TSB tube, was also included in the assay to determine percent inhibition. Percent inhibition was calculated using the formula: (control OD−sample OD)/control OD×100 for each assay time period, and the average between the 5 hr and 10 hr percent inhibition was determined. Results of this are shown in Table 6.

TABLE 6

The Effect of Incubation Time of *Bacillus* isolates on *E. coli* Inhibition

| Producer Incubation Time | 3A-P4 % Inhibition E.20 | 15A-P4 % Inhibition E.20 | 22C-P1 % Inhibition E.20 |
|---|---|---|---|
| 14 h | 12.5 | 7.5 | 7.5 |
| 24 h | 26.3 | 16.3 | 31.3 |
| 36 h | 44.0 | 37.0 | 51.0 |
| 48 h | 6.0 | 9.0 | 21.0 |
| 60 h | 13.0 | 58.4 | 32.0 |
| 72 h | 1.7 | 41.3 | 0. |
| 84 h | 0.0 | 26.1 | 4.4 |

Figure 4:
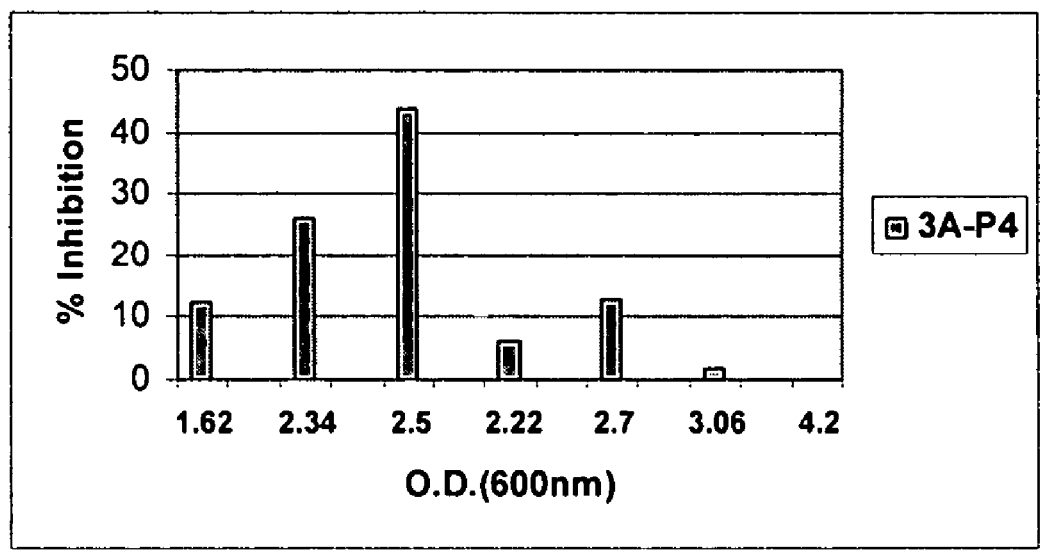
FIG. 4 is a graph showing percent inhibition of *E. coli* strain E.20 by *Bacillus* isolate 3A-P4 at different optical density (OD) readings.
Figure 5:
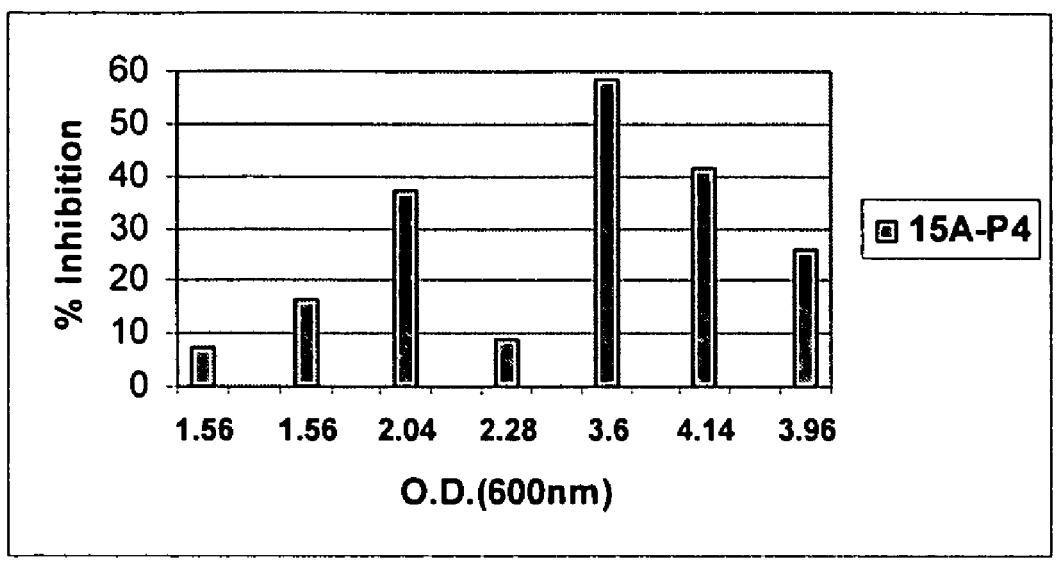
FIG. 5 is a graph showing percent inhibition of *E. coli* strain E.20 by *Bacillus* isolate 15A-P4 at different OD readings.
Figure 6:
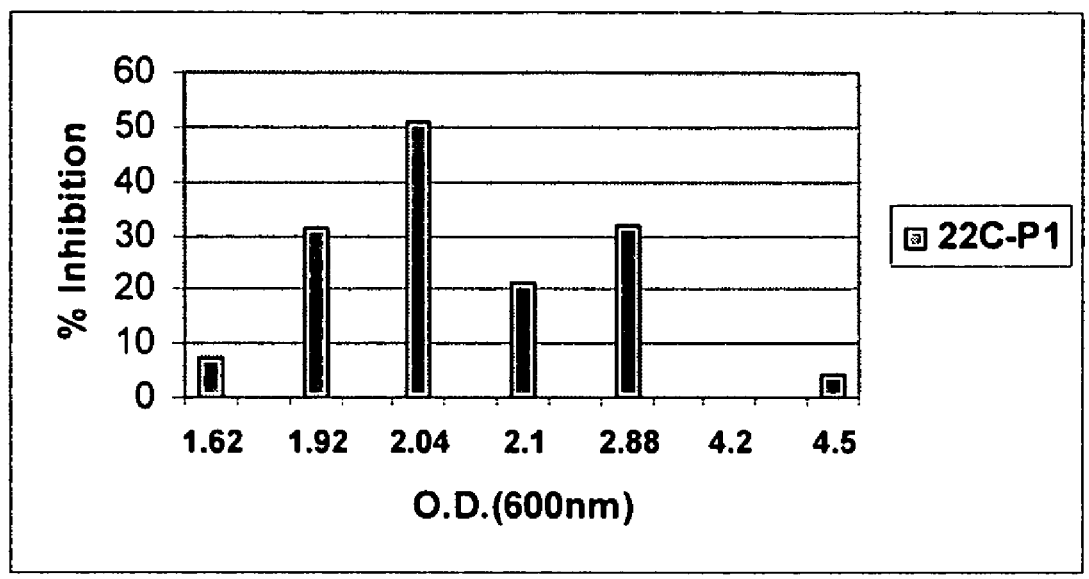
FIG. 6 is a graph showing percent inhibition of *E. coli* strain E.20 by *Bacillus* isolate 22C-P1 at different OD readings.

For growing of the *Bacillus* isolates, the OD that produced an optimal level of inhibition against *E. coli* strain E.20 was also determined. The following ODs were found to produce an optimal active metabolite level: 3A-P4 grown to an OD of 2.5 (FIG. 4), 15A-P4 grown to an OD of 3.6 to 4.15 (FIG. 5), and 22C-P1 grown to an OD of 2.04 (FIG. 6). At these ODs, the active metabolite produced by the *Bacillus* isolates produce the most inhibition against *E. coli*. Therefore, these growth times should correlate to the highest level of active metabolite being formed.

The results obtained determined the time (Table 7) and OD at which the highest percentage of active metabolite was formed for each of the producing strains. This information was used to grow the producing strains for the remainder of the characterization and optimization tests.

TABLE 7

Growth of Active Metabolite Producing *Bacillus* Isolates.

| Producer Growing Time in Hours | 3A-P4 OD (600 nm) | 15A-P4 OD (600 nm) | 22C-P1 OD(600 nm) |
|---|---|---|---|
| 14 | 1.62 | 1.56 | 1.62 |
| 24 | 2.34 | 1.56 | 1.92 |
| 36 | 2.50 | 2.04 | 2.04 |
| 48 | 2.22 | 2.28 | 2.1 |
| 60 | 2.7 | 3.6 | 2.88 |
| 72 | 3.06 | 4.14 | 4.2 |
| 84 | 4.2 | 3.96 | 4.5 |

D. Broth Activity Assay Incubation Time

Incubation trials were performed to determine the time of optimal active metabolite inhibition against *E. coli* using the broth activity assay method. Strains 3A-P4, 15A-P4, and 22C-P1 were used as producer strains, and E.20 and E.23 were used as pathogen indicator strains. The active metabolite was obtained by growing the *Bacillus* strains to their respective ODs and obtaining the crude purified form of the active metabolite as described previously. The crude purified form of the active metabolite was inoculated at 10% into 10 mls of TSB. Pathogen indicator strains were grown as previously described and after reaching an OD of 0.60 (600 nm), were added at 1% to the TSB tubes containing the active metabolite. The assay was incubated at 37° C., and an OD was read at 2, 4, 6, 21, 23, 26, 28, and 30 hours. A control tube with the indicator organism, added at 1% to a 10 ml TSB tube, was also included in the assay to determine percent inhibition and growth pattern. Percent inhibition was calculated as previously described.

Figure 7:
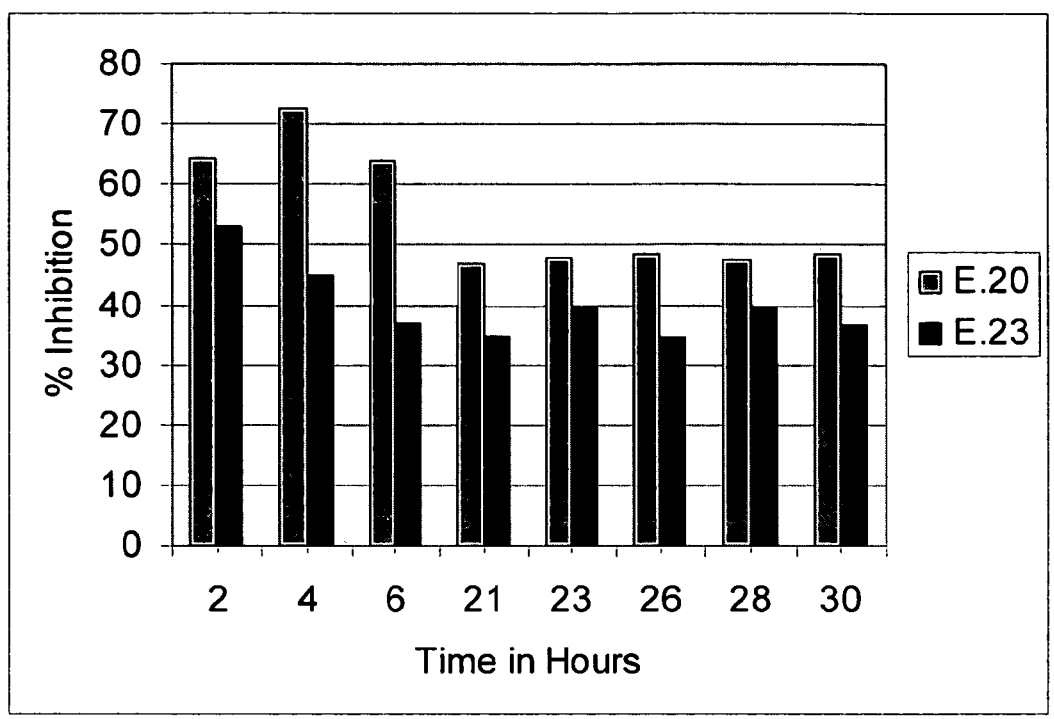
FIG. 7 is a graph showing percent inhibition of *E. coli* strains E.20 and E.23 by *Bacillus* isolate 3A-P4 at different time points.
Figure 8:
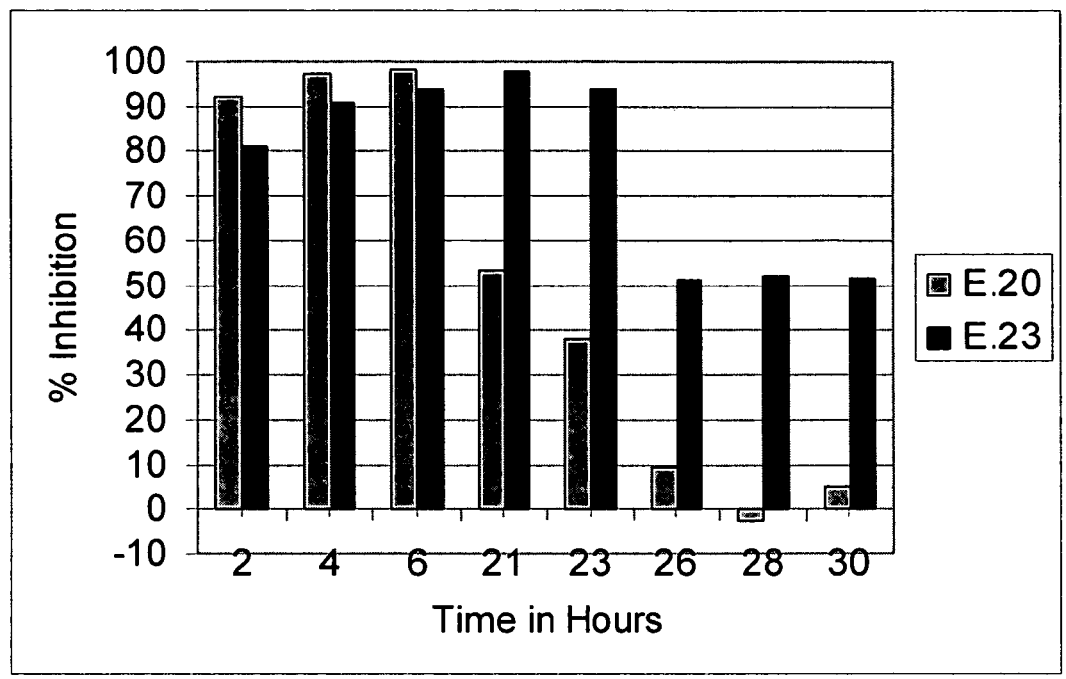
FIG. 8 is a graph showing percent inhibition of *E. coli* strains E.20 and E.23 by *Bacillus* isolate 15A-P4 at different time points.
Figure 9:
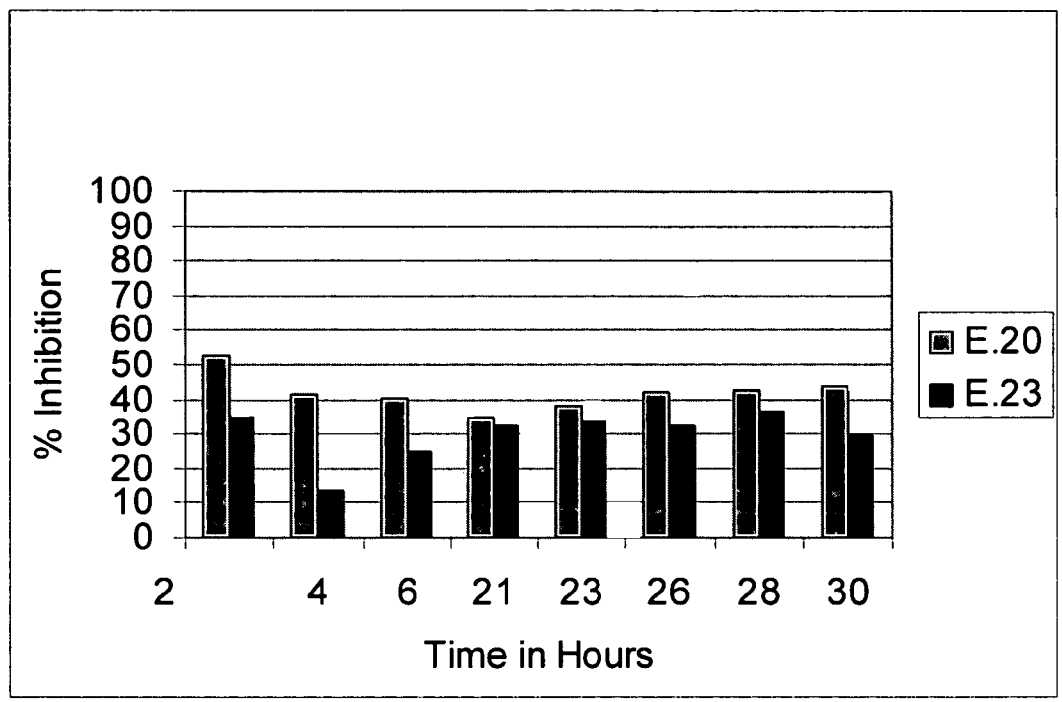
FIG. 9 is a graph showing percent inhibition of *E. coli* strains E.20 and E.23 by *Bacillus* isolate 22C-P1 at different time points.
Figure 10:
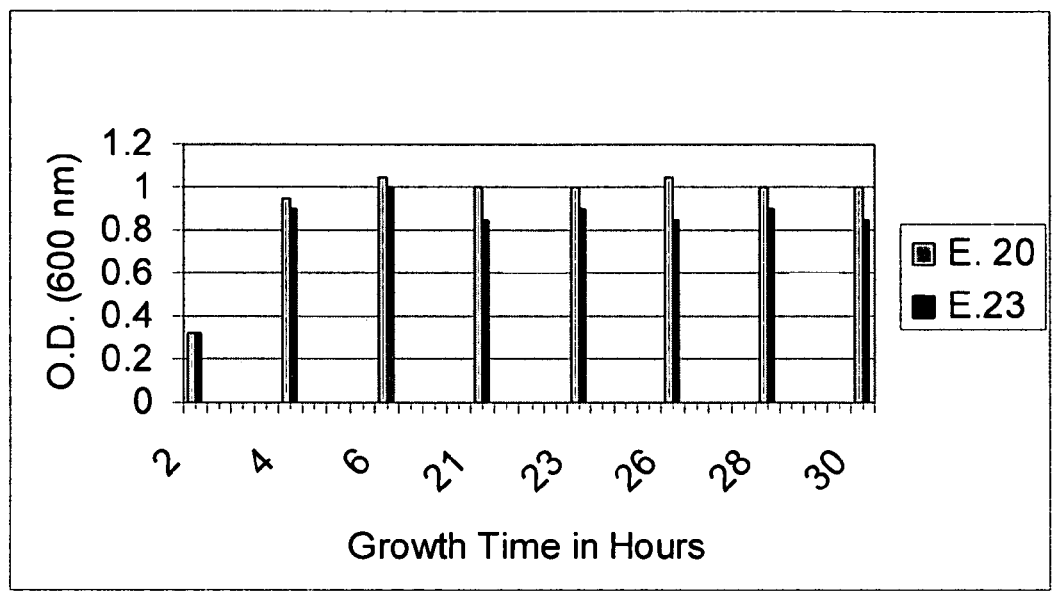
FIG. 10 is a graph showing growth curves, in the absence of any *Bacillus* isolate, of *E. coli* strains E.20 and E.23 at different time points.

Strain 3A-P4 obtained the highest inhibition after four hours (FIG. 7) and, strains 15A-P4 and 22C-P1, after six hours (FIGS. 8 and 9). The *E. coli* growth curve confirmed that between four and six hours of assay time, the *E. coli* was at its highest growth (FIG. 10). Thus, inhibition by the active metabolites is not due to the *E. coli* decreasing naturally.

These results determined the time of highest inhibition of pathogen by the active metabolites. The assay times were used for all the following characterization and optimization tests.

E. Further Purification of Active Metabolite

Ammonium sulfate precipitation was performed on the active metabolites produced by strains 3A-P4, 15A-P4, and 22C-P1. This is a common method for fractioning proteins by precipitation and yields a partially purified protein. The partially purified proteins obtained were utilized in further purification techniques so that a purified protein was achieved. The purified active metabolite yields a better understanding of the microbial inhibition produced by these strains.

Ammonium sulfate concentration fractions must first be determined for each strain to ascertain the amount of ammonium sulfate to add to precipitate the active metabolite. Strains 3A-P4, 15A-P4, and 22C-P1 were grown separately in TSB to their respective OD. Cell free supernatants were obtained by centrifugation at 6000×g for 20 minutes at 4° C. Ammonium sulfate was added to the supernatant in 10% increments until a concentration of 70% is obtained. After the addition of one of the ammonium sulfate concentrations, the supernatant was kept at 4° C. for 2-24 h. The supernatant was harvested by centrifugation at 6000×g for 20 minutes. The supernatant (10 ml) was placed in an Amicon 10,000 MWC centrifugal device and centrifuged at 2000×g until one ml was left in filter. This fraction was then filtered through a 0.2 um filter and tested for activity against *E. coli* using the spot plate method. The pellet obtained from the above centrifugation process was resuspended with 10 ml of Tris-HCl and dialyzed overnight with stirring against 2 liters of the same buffer using a Spectra/Por no. 3 dialysis tubing. It should be noted that instead of dialysis, the pellet sample can also be placed in an Amicon filter and centrifuged at 2000×g until no liquid remains in the filter. Tris-HCl (0.05M)(10 ml) is added to the filter apparatus and centrifuged at 2000×g until no liquid remains in filter. This step is repeated and the filter is centrifuged at 2000×g until one ml is left in filter. The preparation was then filtered through a 0.2 um filter and tested for activity against *E. coli* using the spot plate method. Ammonium sulfate was added to the remainder of the supernatant and the precipitation procedure repeated until the concentration of ammonium sulfate reached 70%.

The ammonium sulfate concentration that precipitates the active metabolite into the pellet after centrifugation is the ammonium sulfate percentage used to partially purify the active metabolite from each strain. Ammonium sulfate concentration needed to precipitate the active metabolite of 15A-P4 is 30%. To decrease unwanted protein and obtain a more partially purified protein it is best to add ammonium sulfate first to the sample at a lower concentration, such as 10%. This precipitates the unwanted protein, leaving the active metabolite in solution. The 30% ammonium sulfate can then be added to precipitate the active metabolite. The supernatant is then collected by centrifugation, as previously described, and the ammonium sulfate concentration needed to precipitate the active metabolite is added.

F. Characterization of the Purified Active Metabolite Produced by 15A-P4 by Gel Electrophoresis:

Strain 15A-P4 was grown to its optimal OD as previously described. The crude form of the active metabolite was obtained as previously described. The active metabolite was then partially purified, after 0.1 mM PMSF and 1.0 M DTT were added to increase protein stability, by performing a 10% and 30% ammonium sulfate precipitation as previously described. The pellet and supernatant fractions from both percentage precipitations were kept and spot plated onto an *E. coli* indicator plate as previously described.

Figure 11:
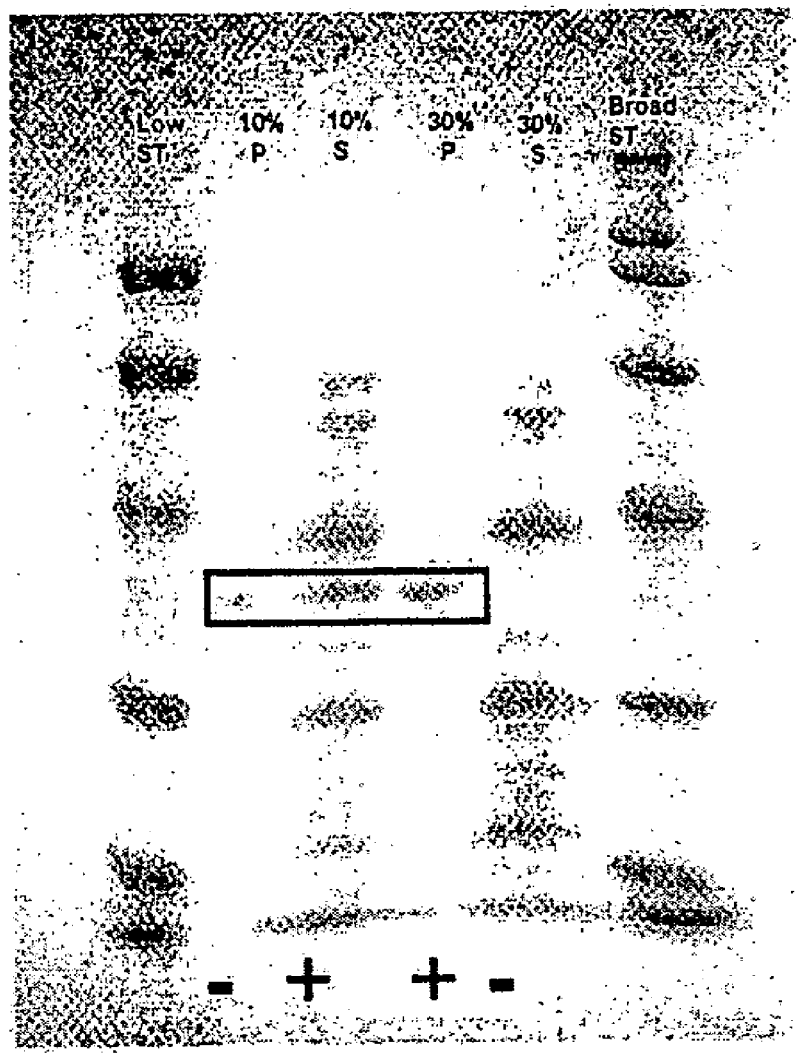
FIG. 11 is a SDS-PAGE on 15A-P4 after ammonium sulfate precipitation. P=pellet fraction, S=supernatant fraction. The box outlines the suspected inhibitory protein located between the 31,000 and 45,000 molecular weight marker. The (+) denotes inhibition of *E. coli* using the spot plate method. The (−) denotes no inhibition of *E. coli* using the spot plate method.

The ammonium sulfate fractions were examined using polyacrylamide gel electrophoresis (PAGE) in the presence of 0.1% sodium dodecyl sulfate (SDS) in a Mini-Protean 3 Cell (Bio-Rad, Hercules, Calif.). The samples were prepared following the protocol provided with the SDS-PAGE molecular weight standards kit (Bio-Rad). A precast 10% polyacrylamide Tris HCl Ready Gel (Bio-Rad) was used. The current was run at 10 mA constant current until the bromphenol blue entered the separating gel. Then the current was increased to 15 mA. The gel was stained using GelCode® Blue stain reagent (Pierce, available from Fisher Scientific, Hampton, N.H.) according to the manufacture's directions. A broad range and low range standard (Bio-Rad) was used that included the following proteins and molecular weights: Myosin (200,000), β-galactosidase (116,250), Phosphorylase b (97,400), Serum albumin (66,200), Ovalbumin (45,000), Carbonic anhydrase (31,000), Trypsin inhibitor (21,500), Lysozyme (14,400), and Aprotinin (6,500). The 10% pellet fraction and the 30% supernatant fraction did not inhibit *E. coli* during the spot inhibition assay. The 10% supernatant and 30% pellet did inhibit *E. coli* during the spot inhibition assay. The pellet and supernatant fractions yielded a band with a molecular weight range between 31,000 and 45,000. Therefore, this band is believed to be the inhibitory protein. (FIG. 11)

G. Characterization of the Active Metabolite Produced by 15A-P4 Using Low Pressure Column Chromatography After ammonium sulfate precipitation, the active metabolite in the 30% pellet fraction was applied to different chemistry columns to determine protein characteristics. The Bio-Rad High Q anion exchange 1 ml cartridge and the Bio-Rad HIC hydrophobic/hydrophilic 1 ml cartridge were explored. To determine characteristics of the protein, 0.5 ml of the active metabolite, after ammonium sulfate precipitation was performed, was mixed with the elution buffer, and was placed on the column. A high salt buffer and low salt buffer were applied to the column to determine under what conditions the active metabolite would adhere to the column. Tris HCl 50 mM with 10 mM NaCl was used as the high salt buffer for the High Q column and Tris HCl 50 mM with 1.0 mM NaCl added was used as low salt buffer for the High Q column. 100 mM sodium phosphate with no salt added was used as the low salt buffer for the HIC column and 100 mM sodium phosphate with 2.4M ammonium sulfate added was used as the high salt buffer for the HIC column. A flow rate of 0.7 ml/min for 25 minutes was used with each buffer. Two large fractions were collected first, one fraction was what came off the column after running a high salt buffer through the column and the other fraction was collected after a buffer containing no salt was ran through the column. These fractions were then concentrated using the Amicon centrifugal device by placing the fractions in a 10,000 MWC Amicon centrifugal device and spun at 3000 rpm until dry. Two buffer washes were performed, and the protein was reconstituted to 300 μl.

With the HIC column, the fraction collected during the high salt buffer application yielded a positive inhibition with the spot plate assay. The separation principle behind the HIC column is not yet fully understood. All theories support that interaction is related to the hydrophobic surface area found on all proteins and that it is increased by high ionic strength and high temperature (11). Therefore, the fact that the protein eluted with a high concentration of salt leads to suspect that the protein is hydrophilic in nature.

With the High Q anion exchange column, both the high salt buffer fraction and the no salt buffer fraction yielded no inhibition on the spot plate assay. The procedure was repeated and nine fractions were collected after a high salt buffer was applied and nine fractions were collected after a no salt buffer was applied. Three of the fractions collected with the salt buffer showed inhibition on the spot plate assay. These three fractions also had 60->100 mg/dl of protein using the protein determination test. None of the fractions from the no salt buffer showed inhibition, but two fractions had 20-30 mg/dl of protein. Therefore, the fact that the protein eluted from an anion column with a high concentration of salt demonstrates that the protein is a cation.

In summary, it was discovered that the active metabolite produced by strain 15A-P4 has a molecular weight between 31,000 and 45,000, is a cation, and appears to be hydrophilic.

Example 10

Determination of Stability of the Active Metabolites Produced by 3A-P4, 15A-P4, and 22C-P1

The stability of the active metabolite of the *Bacillus* isolates was assessed. This information also helps to characterize the active metabolites. Assays were performed using the crude form of the active metabolite to determine enzyme degradation, heat stability, and mode of action. The activity of the active metabolite was determined after exposure to enzymes and heat.

A. Enzyme Degradation Assay

Enzyme degradation trials were performed on strains 3A-P4, 15A-P4, and 22C-P1 to determine if the active metabolite formed was a protein. Producers were grown in TSB as previously described, and the active metabolite was obtained in the crude purified form.

Enzymes (all obtained from Sigma, St. Louis, Mo.) used were: α-chymotrypsin, pronase E, proteinase K, pepsin, trypsin, and catalase. Two hundred and fifty milligrams of each enzyme was added to 100 ml of sterile cold distilled water and kept on ice before use. 1 ml of each enzyme was separately added to 4 mls of the crude purified active metabolite for a final concentration of 500 μg/ml. After incubated at 37° C. for 60 minutes, each sample was assayed for bacteriocin activity using the broth activity assay method. Samples without enzymes were used as controls.

The enzyme treated active metabolite was added to a 10 ml TSB tube at 10%. Strain E.23 was used as the indicator organism and was grown as previously described. The indicator was then added to the TSB tubes, which contained the active metabolite, at a 1% concentration. Samples without enzyme-treated active metabolites and samples without active metabolites were used as controls. Percent inhibition was determined as previously described.

The active metabolite produced by strain 3A-P4 was found to be sensitive to α-chymotrypsin, pepsin, catalase, and pronase E but not affected by trypsin or proteinase K. Active metabolite produced by strain 15A-P4 was found to be sensitive to catalase and pronase E but not affected by α-chymotrypsin, pepsin, trypsin, or proteinase K. The active metabolite produced by strain 22C-P1 was found to be sensitive to trypsin and pronase E but not affected by α-chymotrypsin, pepsin, catalase, or proteinase K.

B. Heat Assay

The temperature sensitivity of the crude purified active metabolites produced by strains 3A-P4, 15A-P4, and 22C-P1 were examined. The isolates were grown as previously indicated and the crude active metabolite was obtained. The active metabolites were heated to 100° C. for 1, 5, 10, and 15 minutes; cooled to room temperature; and inoculated at 10% into 10 ml of TSB. The active metabolites were also autoclaved for 20 minutes at 121° C. and assayed for inhibitory activity. Strain E.23 was used as the indicator organism and was grown as previously described and inoculated at 1% into the 10 ml of TSB containing the active metabolite. The assay was incubated at 37° C. and OD read at either four or six hours. Percent inhibition was calculated as previously described.

All three of the active metabolites' activity was reduced after heat treatment (Table 8). But all three active metabolites still had some inhibitory activity after heat treatment.

obtained as previously described. E. coli strains E.20 and E.23 were grown as previously described.

The active metabolite of each strain was tested separately and added at 10% to a 10 ml TSB tube. Strains E.20 and E.23 were added separately at 1% to the TSB tube containing the active metabolite. A TSB tube inoculated with only E.20 or E.23 at 1% was used as the control. The tubes were incubated at 37° C., and an OD (600 nm) was obtained every two hours for a total of eight hours. Time zero values were also obtained. To obtain live E. coli counts from the inoculated TSB tubes plating was performed. Serial dilutions were made every two hours for a total of eight hours and plated on TSA and incubated at 37° C. overnight. Time zero values were also obtained. The plates were counted after 24 h of incubation.

Figure 13A:
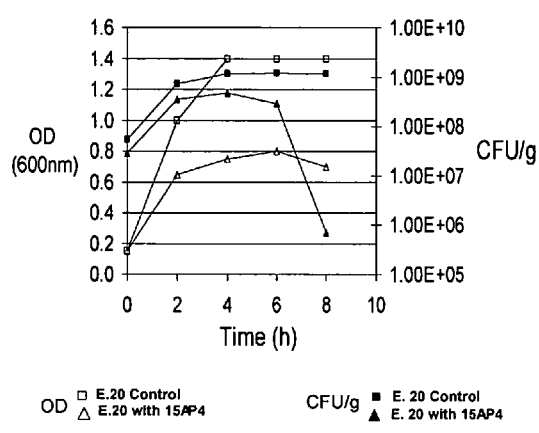
FIGS. 13A and 13B are the graphs showing the mode of action of the active metabolite produced by 15A-P4 on *E. coli* strain E.20 (FIG. 13A) and *E. coli* strain E.23 (FIG. 13B).
Figure 13B:
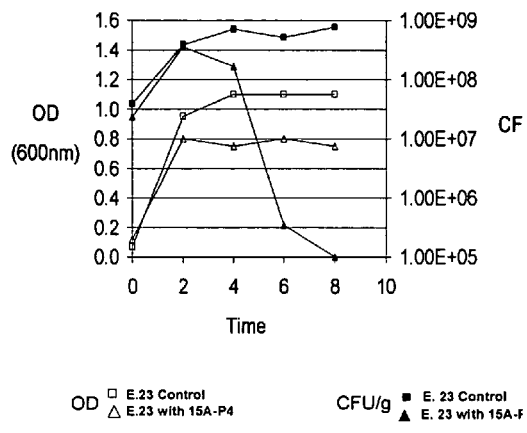
Figure 14A:
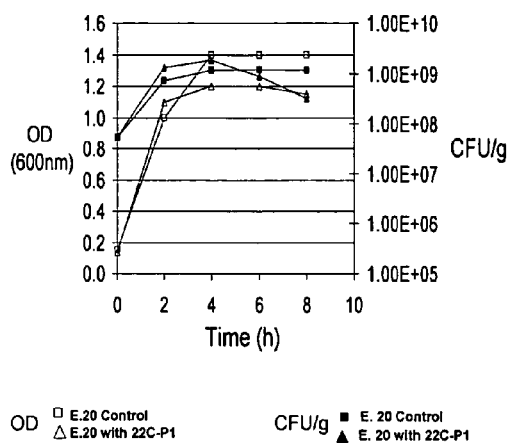
FIGS. 14A and 14B are graphs showing the mode of action of the active metabolite produced by 22C-P1 on *E. coli* strain E.20 (FIG. 14A) and *E. coli* strain E.23 (FIG. 14B).
Figure 14B:
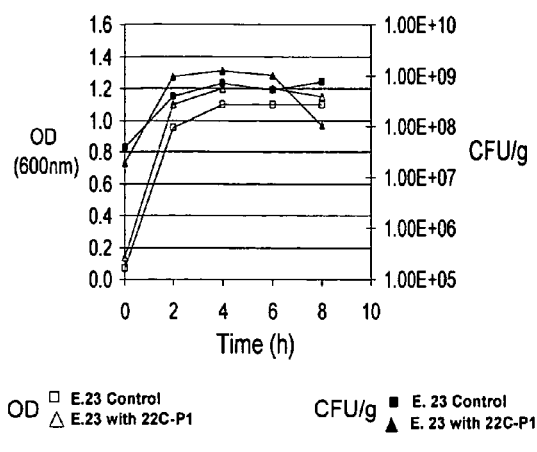

Strain 3A-P4 active metabolite decreased E. coli counts for both E. coli strain E.20 (FIG. 12A) and strain E.23 (FIG. 12B) by one log and decreased the OD values. Strain 15A-P4 active metabolite decreased E. coli counts for both E. coli strain E.20 (FIG. 13A) and strain E.23 (FIG. 13B) by three to four logs and also decreased the OD values. Strain 22C-P1 active metabolite decreased E. coli counts for both E. coli strain E.20 (FIG. 14A) and strain E.23 (FIG. 14B) by half a log to one log and also decreased the OD values. The results indicate that 15A-P4 active metabolite is bactericidal, and 3A-P4 and 22C-P1 active metabolites are at least bacteriostatic. Strains 3A-P4 and 22C-P1 active metabolites may also prove to be bactericidal if the assay was allowed to continue longer.

Example 11

A. Media Optimization

Strains 3A-P4, 15A-P4, and 22C-P1 were grown in different media to determine a media that would yield the highest cell and spore growth. The protein found in TSB was substituted at different percentage levels with other proteins. Carbohydrates and minerals, common to industry, were also included in the different media at different percentage levels.

Strains 3A-P4, 15A-P4, and 22C-P1 were inoculated into the above different media and grown at 32° C. with shaking.

TABLE 8

Percent inhibition of 3A-P4, 15A-P4, and 22C-P1 after heat treatments.

| | 3A-P4 % Inhibition | | 15A-P4 % Inhibition | | 22C-P1 % Inhibition | |
|---|---|---|---|---|---|---|
| | Heat Treated | No Heat | Heat Treated | No Heat | Heat Treated | No Heat |
| 1 Min 100° C. | 100 | 100 | 94.4 | 100 | 88.3 | 100 |
| 5 Min. 100° C. | 75 | 100 | 87.6 | 100 | 56.3 | 100 |
| 10 Min. 100° C. | 50 | 100 | 75.3 | 100 | 46.2 | 100 |
| 15 Min. 100° C. | 50 | 100 | 62.0 | 100 | 25.7 | 100 |
| Autoclaved | 32.4 | 100 | 36.7 | 100 | 20.5 | 100 |

C. Mode of Action

Tests were performed to determine if the active metabolites produced by strains 3A-P4, 15A-P4, and 22C-P1 were bactericidal or bacteriostatic to E. coli. Strains 3A-P4, 15A-P4, and 22C-P1 were grown to their optimal OD as previously described. The crude form of the active metabolite was Samples for spore yield were aseptically removed at 24 and 48 h. The sample was placed in a 63° C. water bath for 35 minutes to kill all vegetative cells. Spores were enumerated by plating serial dilutions on TSA, which were incubated for 24 hours at 32° C. Cells were enumerated by plating serial dilutions on TSA of the culture at 24 h and 48 h, which were also incubated for 24 at 32° C. The media that yielded the highest cell and spore growth for each strain is listed below.

B. Media Yielding Highest Cell and Spore Growth

For 3A-P4, growth media was Primagen 2%, Sucrose 5 g/L, Dipotassium phosphate 2.5 g/L, 0.5 g/L, $MgSO_4 7H_2O$, 0.12 g/L, $FeSO_4 7H_2O$, 0.05 g/L, $MnSO_4 H_2O$, 0.004 g/L, $Zn SO_4 7H_2O$, and 0.05 g/L CaCl. Growth conditions were: 32° C. with shaking for 48 hours to obtain a spore count of at least $1 \times 10^9$.

For 15A-P4, growth media was peptonized milk protein 5%, Dextrose 2.5 g/L, Dipotassium phosphate 2.5 g/L, 0.5 g/L $MgSO_4 7H_2O$, 0.12 g/L $FeSO_4 7H_2O$, 0.05 g/L $MnSO_4 H_2O$, 0.004 g/L $Zn SO_4 7H_2O$, and 0.05 g/L CaCl. Growth conditions were 32° C. with shaking for 48 hours to obtain a spore count of at least $1 \times 10^9$.

For 22C-P1, growth media was Primagen, 2%, Dextrose 2.5 g/L, Dipotassium phosphate 2.5 g/L, 0.5 g/L $MgSO_4 7H_2O$, 0.12 g/L $FeSO_4 7H_2O$, 0.05 g/L $MnSO_4 H_2O$, 0.004 g/L $Zn SO_4 7H_2O$, and 0.05 g/L CaCl. Growth conditions were 32° C. with shaking for 48 hours to obtain a spore count of at least $1 \times 10^9$. Primagen and peptonized milk protein obtained from Quest International, Hoffman Estates, Ill.

Example 12

Field Trial A

The objective of Field Trial A was to evaluate the ability of the selected *Bacillus* strains to reduce the incidence of *E. coli* disease and to improve performance in the nursery phase.

The site is located approximately 7 miles east of Pipestone, Minn. It was a farrow to finish farm with an *E. coli* mortality of 20% without vaccine and antibiotic use. The intervention of vaccines and antibiotics had decreased the *E. coli* mortality to 5-10%.

The farm consisted of one nursery barn with two rooms. Each room had two rows of six pens with each pen holding 25 pigs. Each room had a capacity of holding 300 pigs. Pigs remained in the nursery on an average of 28 days before being moved to the finishing facility.

The pigs were weaned at 26 days of age and were sorted by sex and assigned to one of three weight classes (light, medium and heavy). Control and treated pigs were placed in separate rows to decrease the possibility of cross over contamination between treated and control pigs of the *Bacillus* strains fed to the treated pigs. Each row had three pens of gilts and three pens of barrows with one light, one medium, and one heavy weight group in each sex.

The *E. coli* vaccine was given to all weaned pigs. Several injectable antibiotics (gentamicin, enrofloxacin) were given to both control and treated pigs when scouring was observed.

The treated pigs received Product 1 in a basemix form, containing *Bacillus* strains and carriers as follows: 30% 3A-P4, 60% 15A-P4, 10% 22C-P1 at a final product count of $3.0 \times 10^7$ cfu/g and 40% rice hulls, 19% dried brewers grain, 40% limestone, and 1% baylith. The basemix was then added to the standard farm pellet diet and grind and mix diet at the rate of 5 lbs/ton of feed to make the final *Bacillus* inclusion rate $7.35 \times 10^4$ cfu/g. The pellet diet was started on day one post-weaning, and Product 1 was continued in all diet phases until the end of the nursery stage. The control pigs received the same pelleted and grind and mix diets as the treated pigs except they were devoid of the *Bacillus* strains.

Included in the nursery pellet diet for control and treated pigs was the antibiotic ASP-250. All the grind and mix rations for both control and treated pigs included BMD and 3-Nitro. Normal protocol was utilized for pig management.

Mortality and disease incidence was recorded weekly in both the treated and control pigs. Pen weight, pen sex, and number of pigs in pen were recorded on day one and day 28 of the field trial.

Before the field trial began environmental, rectal, and fecal swabs were obtained from the nursery. *E. coli* strains from the swabs were grown and isolated at Agtech Products and kept frozen for future use. Multiplex PCR was used to determine if a strain was pathogenic.

All pathogenic *E. coli* isolates were individually tested in vitro against the three *Bacillus* strains included in Product 1. This was done using broth activity assay. Each active metabolite produced by the *Bacillus* in Product 1 was tested against each pathogenic *E. coli* strain found on the farm using the broth activity assay to obtain percent degree of inhibition. The degree of inhibition was monitored by way of optical density readings using a spectrophotometer. Results of the degree of inhibition are shown below in Table 12.

Feeding Product 1 to nursery pigs during Field Trial A decreased mortality. Mortality in the control pigs remained high at 7.0%, however, mortality in the pigs fed Product 1 decreased to 1.4%. Pigs had typical symptoms of *E. coli* disease, as seen previously and diagnosed on this farm. Therefore, the cause of mortality was determined to be attributed to *E. coli* disease. No improvement in performance was seen during this trial. Treated pigs gained an average of 17.45 lbs per pig, and control pigs gained an average of 18.98 lbs per pig (Tables 9 and 10).

TABLE 9

Effect of Product 1 during Field Trial A.

|  | Treated Group | Control Group |
|---|---|---|
| Pig Number In | 139 | 143 |
| Pig Number Dead | 2 | 10 |
| Percent Mortality | 1.4 | 7.0 |

TABLE 10

Results of Feed Trial A.

| Pen No. | Treated Or | Gilt or Barrow | Weaning age | Date in | Pig # | Pen Weight | Date Out | Pig # | Pen Weight | # dead | Weight Gained/pig |
|---|---|---|---|---|---|---|---|---|---|---|---|
| 1 | T | B | 26-28 | May 21, 2002 | 23 | 584 | Jun. 18, 2002 | 23 | 1096 |  | 22.3 |
| 2 | T | B | 26-28 | May 21, 2002 | 24 | 479 | Jun. 18, 2002 | 24 | 877 |  | 16.6 |
| 3 | T | B | 26-28 | May 21, 2002 | 24 | 425 | Jun. 18, 2002 | 23 | 816 | 1 | 17.8 |
| 4 | T | G | 26-28 | May 21, 2002 | 23 | 394 | Jun. 18, 2002 | 23 | 729 |  | 14.6 |
| 5 | T | G | 26-28 | May 21, 2002 | 22 | 326 | Jun. 18, 2002 | 22 | 729 |  | 18.3 |
| 6 | T | G | 26-28 | May 21, 2002 | 23 | 256 | Jun. 18, 2002 | 22 | 573 | 1 | 14.9 |

TABLE 10-continued

Results of Feed Trial A.

| Pen No. | Treated Or | Gilt or Barrow | Weaning age | Date in | Pig # | Pen Weight | Date Out | Pig # | Pen Weight | # dead | Weight Gained/pig |
|---|---|---|---|---|---|---|---|---|---|---|---|
| 7  | C | B | 26-28 | May 21, 2002 | 24 | 290 | Jun. 18, 2002 | 24 | 574 |   | 11.8 |
| 8  | C | B | 26-28 | May 21, 2002 | 24 | 372 | Jun. 18, 2002 | 23 | 803 | 1 | 19.4 |
| 9  | C | B | 26-28 | May 21, 2002 | 25 | 425 | Jun. 18, 2002 | 24 | 869 | 1 | 19.2 |
| 10 | C | G | 26-28 | May 21, 2002 | 23 | 404 | Jun. 18, 2002 | 22 | 805 | 1 | 19.0 |
| 11 | C | G | 26-28 | May 21, 2002 | 24 | 497 | Jun. 18, 2002 | 22 | 902 | 2 | 20.3 |
| 12 | C | G | 26-28 | May 21, 2002 | 23 | 540 | Jun. 18, 2002 | 18 | 859 | 5 | 24.2 |

One hundred swabs were collected from the nursery. From the 100 swabs, 100 *E. coli* isolates were tested to determine their pathogenicity using the multiplex PCR procedure. Fifty-three of the 100 isolates were found to contain one or more genes associated with pathogenicity. The genotypes and the results of the inhibition of the *E. coli* isolates by the *Bacillus* in Product 1 are shown below in Table 11. All the *E. coli* isolates were inhibited by all three *Bacillus* strains ranging from 18.2 to 96% inhibition of growth. Strain 15A-P4 demonstrated the most effective inhibition against pathogenic *E. coli* isolated from Field Trial A.

In Field Trial A, feeding Product 1 to nursery swine throughout the nursery period decreased mortality due to *E. coli* disease. Product I did not enhance nursery swine performance in Field Trial A. The fact that performance was not enhanced in this trial may be due to the fact that in our laboratory testing we confirmed that ASP-250, which was included in the nursery pellet diet for control and treated pigs, is bactericidal to the *Bacillus* strains included in Product 1. This is most likely due to the sulfamethazine portion of this antibiotic. Penicillin and aureomycin (chlortetracycline) have been shown in laboratory testing not to have little effect on the *Bacillus* strains in Product 1.

TABLE 11

Characterization of pathogenic *E. coli* isolates from Field Trial A.

| E. coli Sample | Source of sample | Multiplex Results | Bacillus Strain 3A-P4 | Bacillus Strain 15A-P4 | Bacillus Strain 22C-P1 |
|---|---|---|---|---|---|
| E. 271 | Fecal | STb | 60.0 | 91.5 | 55.0 |
| E. 273 | Fecal | STa | 45.2 | 82.7 | 64.0 |
| E. 274 | Fecal | STb | 44.2 | 84.2 | 60.0 |
| E. 276 | Fecal | K88 | 46.2 | 95.0 | 52.0 |
| E. 278 | Fecal | F18, STX2e, STa, STb | 41.7 | 87.1 | 35.0 |
| E. 279 | Fecal | F18, STX2e, STa, STb | 36.8 | 86.5 | 37.5 |
| E. 284 | Fecal | STb | 44.0 | 85.8 | 53.8 |
| E. 285 | Fecal | K88 | 38.0 | 86.4 | 51.9 |
| E. 294 | Fecal | F18, STX2e, STa, STb | 42.1 | 92.8 | 22.5 |
| E. 311 | Fecal | STb | 42.0 | 86.7 | 51.9 |
| E. 315 | Fecal | STb | 39.6 | 86.9 | 47.9 |
| E. 317 | Fecal | STb | 48.0 | 78.8 | 53.6 |
| E. 318 | Fecal | K88 | 50.0 | 88.8 | 50.0 |
| E. 319 | Fecal | F18, STX2e, STa, STb | 36.1 | 88.8 | 36.8 |
| E. 320 | Fecal | K88 | 45.8 | 88.8 | 50.0 |
| E. 323 | Fecal | STb | 47.9 | 90.8 | 57.4 |
| E. 324 | Rectal | K88 | 58.3 | 96.8 | 55.8 |
| E. 325 | Rectal | STb | 51.9 | 88.8 | 61.4 |
| E. 327 | Rectal | K99, STa | 65.0 | 92.7 | 31.8 |
| E. 328 | Rectal | K99, STa | 55.0 | 90.4 | 38.5 |
| E. 329 | Rectal | K99, STa | 59.1 | 90.9 | 41.7 |
| E. 337 | Rectal | F18, STX2e, STa, STb | 41.2 | 90.0 | 23.7 |
| E. 361 | Rectal | F18, STX2e, STa, STb | 36.8 | 92.4 | 25.0 |
| E. 374 | Environment | F18, STX2e, STa, STb | 47.4 | 91.9 | 25.0 |
| E. 378 | Environment | F18, STX2e, STa, STb | 37.5 | 89.5 | 18.2 |
| E. 379 | Environment | F18, STX2e, STa, STb | 31.8 | 87.3 | 21.7 |

Example 13

Field Trial B-1 and B-2

The objective of Field Trial B-1 and B-2 was to develop a feed additive product containing biologically-active active metabolites from *Bacillus* capable of enhancing the performance of swine by reducing intestinal pathogens such as *E. coli*.

The site for Field Trial B-1 and B-2 was a farrow to finish facility located approximately 7 miles east of Pipestone, Minn. (Same site used in Example 12). A new nursery to finish facility was built in the spring of 2003. Field Trials B-1 and B-2 were performed in this new facility. No *E. coli* disease was evident in the new facility.

The new facility consisted of four rooms with two large pens in each room capable of housing pigs from the nursery phase through the finishing phase. For our trials, the pens in each room were divided down the middle to make four smaller pens. Each pen could hold on the average 70 pigs.

The pigs were weaned at 18-21 days of age and were sorted by sex to one of the treatment groups. The control and treated group was comprised of one pen of barrows and one pen of gilts. The pigs remained in the study for 28 days.

The treated pigs received Product 2 in a basemix form containing *Bacillus* strains and carriers as follows: 100% 22C-P1 at a final product count of $3.0 \times 10^8$ cffu/g and 40% rice hulls, 19% distilled brewers grain, 40% limestone, and 1% baylith. The basemix was then added to the standard farm pellet diet and grind and mix diet at the rate of 5 lbs/ton of feed to make the final *Bacillus* inclusion rate $7.35 \times 10^5$ CFU/g of feed. The pellet diet was started on day one post-weaning, and Product 2 was continued in all diet phases until the end of the nursery stage. The control pigs received the same pelleted and grind and mix diets as the treated pigs except they were devoid of the *Bacillus* strain.

The pellet diet was devoid of antibiotics. And all the grind and mix rations for both control and treated pigs included BMD, 3-Nitro, and CTC. Normal protocol was utilized for pig management.

Mortality and disease incidence was recorded weekly in both the treated and control pigs. Pen weight, pen sex, and number of pigs in pen were recorded on day one and day 33 (Field Trial B-1) and day 31 (Field Trial B-2) of the field trial.

Feeding Product 2 to nursery pigs during Field Trials B-1 and B-2 increased performance. In Field Trial B-1 weight gained per pig and average daily gain (ADG) was 11.3% higher in pigs fed Product 2. In Field Trial B-2 weight gained per pig was 3.9% higher in pigs fed Product 2, and ADG was 4.0% higher in pigs fed Product 2. The overall effect is summarized in Table 12. *E. coli* disease did not occur during these trials; therefore mortality due to *E. coli* was not analyzed.

TABLE 12

Overall effect of Product 2 for Field Trials B-1 and B-2.

|  | Treated Group | Control Group | % Difference |
| --- | --- | --- | --- |
| Weight gained/pig | 23.48 | 21.8 | 7.71 |
| ADG | 0.737 | 0.683 | 7.91 |

In Field Trials B-1 and B-2, feeding Product 2 to nursery swine throughout the nursery period increased ADG by 7.9% and weight gained per pig by 7.7%. Product 2 was effective at enhancing nursery swine performance in Field Trials B-1 and B-2.

Example 14

Field Trial C

The objective of Field Trial C was to evaluate the ability of the selected *Bacillus* strains to reduce the incidence of *E. coli* disease and to improve performance in the nursery phase.

The field trial site is located approximately 7 miles east of Pipestone, Minn. It was a nursery and finish farm with an *E. coli* mortality of 15% without vaccine and antibiotic use. The intervention of vaccines and antibiotics had decreased the *E. coli* mortality to 3-5%.

The farm consisted of two nursery barns with two rooms in each barn. Each room had four rows of six pens with each pen holding 25 pigs. Each room had a capacity of holding 600 pigs. Pigs remained in the nursery for 7-8 weeks before being moved to the finishing facility.

Pigs were placed in the nursery at 16-18 days of age upon arriving at the farm and were sorted by sex and assigned to one of two weight groups (light and heavy pigs). Control pigs were placed in one room and treated pigs in the other room to minimize the chance for *Bacillus* cross contamination. The *E. coli* vaccine was given to control pigs only.

The treated pigs received Product 1 described in Example 12 in both the standard farm pellet diet and in the grind and mix diet at $7.35 \times 10^4$ cfu/g inclusion rate. The pellet diet was started upon placement, and Product 1 was continued in all diet phases until the end of the nursery stage. The control pigs received the same pelleted and grind and mix diets as the treated pigs except they were devoid of the *Bacillus* strains. None of the diets included antibiotics aimed at treating *E. coli* disease. Normal protocol was utilized for pig management.

Mortality and disease incidence was recorded weekly in both the treated and control pigs. Room weight was recorded upon placement of pigs and at the end of the field trial.

Before the field trial began environmental, rectal, and fecal swabs were obtained from the nursery. Strains from the swabs were grown and isolated at Agtech Products and kept frozen for future use. Multiplex PCR was used to determine if a strain was pathogenic.

All pathogenic *E. coli* isolates were individually tested in vitro against the three *Bacillus* strains included in Product 1. This was done using broth activity assay. Each active metabolite produced by the *Bacillus* in Product 1 was tested against each pathogenic *E. coli* strain found on the farm using the broth activity assay to obtain percent degree of inhibition. The degree of inhibition was monitored by way of optical density readings using a spectrophotometer.

Twenty days into the field trial challenges from pathogenic *E. coli* resulted in a death loss of 0.50%-0.75% in the pigs fed Product 1 compared to a death loss of 3.0%-5.0% for pigs fed the control diet (no Product 1). Shortly after this period a *S. suis* infection became a major challenge at this farm and subsequent deaths were diagnosed at necropsy as *S. suis*.

One hundred swabs were collected from the nursery. From the 100 swabs, 100 *E. coli* isolates were tested using multiplex PCR procedure to identify pathogenic strains. Thirty-one of the 100 isolates were found to be pathogenic. Genotypes for each of the 31 isolates and the results of the inhibition of the *E. coli* by the *Bacillus* in Product 1 are shown in Table 13. All the *E. coli* isolates were inhibited by all three *Bacillus* strains ranging from 6.9 to 96% inhibition of growth. Strain 15A-P4 demonstrated the most effective inhibition against pathogenic *E. coli* isolated from Field Trial C.

TABLE 13

Characterization of the pathogenic E. coli isolates from Field Trial C.

| E. coli | Sample | Multiplex Results | Bacillus Strain 3A-P4 | Bacillus Strain 15A-P4 | Bacillus Strain 22C-P1 | |
|---|---|---|---|---|---|---|
| E. 54 | Rectal | F18 | 83.5 | 98.5 | 19.2 | |
| E. 55 | Rectal | K88 | 80.7 | 95.7 | 14.3 | |
| E. 57 | Rectal | STb | 97.7 | 99.2 | 52.1 | |
| E. 66 | Fecal | K88 | 69.0 | 91.0 | 19.2 | |
| E. 67 | Fecal | K88 | 58.6 | 96.3 | 16.7 | |
| E. 69 | Fecal | K88 | 60.0 | 80.5 | NA | |
| E. 74 | Environment | K88 | 53.8 | 95.5 | 6.9 | |
| E. 86 | Rectal | F18 | 91.0 | 95.8 | NA | |
| E. 87 | Fecal | STa, STb, K88, STx2e | 66.0 | NA | NA | |
| E. 90 | Fecal | F18 | 64.6 | 97.9 | 20.7 | |
| E. 91 | Fecal | F18 | 75.4 | 97.9 | 15.5 | |
| E. 96 | Fecal | K88 | 79.2 | 89.1 | NA | |
| E. 104 | Rectal | STb | 92.2 | 95.2 | 37.0 | |
| E. 106 | Rectal | F18 | 89.5 | 96.4 | NA | |
| E. 110 | Fecal | Sta | 79.1 | 79.2 | NA | |
| E. 115 | Fecal | STa, STb, F18, STx2e | 58.9 | 85.3 | 15.0 | |
| E. 116 | Fecal | STa, STb, F18, STx2e | 50.0 | 85.0 | 22.0 | |
| E. 117 | Fecal | STb | 57.7 | 93.0 | 16.7 | |
| E. 118 | Fecal | K88 | 65.4 | 95.8 | 16.7 | |
| E. 123 | Environment | STa, STb, F18, STx2e | 37.0 | 63.1 | 24.0 | |
| E. 239 | Environment | K88 | 93.9 | 95.8 | 15.0 | |
| E. 240 | Fecal | Sta | 56.5 | 99.0 | 33.0 | |
| E. 241 | Rectal | F18, STx2e, STb | 83.3 | 98.2 | NA | |
| E. 246 | Fecal | K88 | 53.8 | 94.2 | 35.7 | |
| E. 247 | Fecal | Sta | 33.3 | 98.9 | 28.6 | |
| E. 251 | Fecal | K88, STa | 39.3 | 90.7 | 23.5 | |
| E. 252 | Fecal | F18 | 97.7 | 99.2 | 30.0 | |
| E. 256 | Rectal | K88 | 59.2 | 92.8 | 30.0 | decreased |
| E. 257 | Environment | K88, STx2e, STb | 66.3 | 98.5 | 28.6 | |
| E. 265 | Fecal | K88 | 81.4 | 96.7 | 12.5 | |
| E. 268 | Fecal | F18 | 96.3 | 99.2 | 25.0 | |

In Field Trial C, feeding Product 1 to nursery swine throughout the nursery period mortality due to E. coli disease. During Field Trial C, Product 1 did not enhance nursery swine performance. The lack of an improvement in performance may have been due to disease issues caused by other microorganisms, such as S. suis, and management issues.

Example 15

Field Trial D

The objective of Field Trial D was to evaluate the ability of the selected Bacillus strains to reduce the incidence of E. coli disease in the nursery phase. The site is located in Indiana. It is a 2000 sow farrow to finish farm. E. coli had been diagnosed previously by the veterinarian.

The farm has multiple nurseries. The study was performed at the Wendell Cates nursery. The rooms consisted of two rows of 12 pens with approximately 20 pigs per pen. Pigs remained in the nursery on an average of 35 days before being moved to the finishing facility.

The pigs came into the nursery between 11 and 13 pounds and were sorted by weight into three groups—light, medium, and heavy. Control pigs (403 head) were placed in one room and treated pigs (440 head) in another room to minimize the chance for Bacillus cross contamination.

Treated and control pigs received penicillin in the water for coughing. The control pigs received gentamycin in the water for scours.

The treated pigs received Product 3 in a basemix form containing Bacillus strains and carriers as follows: 10% of the total count of strain 15A-P4, 90% of the total count of strain 22C-P1 at a final product count of $3.0 \times 10^8$ cfu/g and 40% rice hulls, 19% dried brewers grain, 40% limestone, and 1% baylith. The basemix was then added to the standard farm pellet diet and grind and mix diet at the rate of 5 lbs/ton of feed to make the final Bacillus inclusion rate $7.35 \times 10^5$ cfu/g of feed. Product 3 was added to both the standard farm pellet diet and in the grind and mix diet at $7.35 \times 10^5$ CFU/g inclusion rate. The pellet diet was started on day one post-weaning, and Product 3 was continued in all diet phases until the end of the nursery stage. The control pigs received the same pelleted and grind and mix diets as the treated pigs except they were devoid of the Bacillus strains. Normal protocol was utilized for pig management.

Mortality and disease incidence, and pig numbers going into the trial and into the finisher were recorded.

Rectal and fecal swabs were obtained from the nursery during an E. coli outbreak. Three swabs were from treated pigs and three swabs came from control pigs. E. coli strains were grown and isolated at Agtech Products and kept frozen for future use. Multiplex PCR was used to determine if a strain was pathogenic.

Treated pigs had a total death loss of 4.1%. Death loss due to *E. coli* disease/scours was 1.4%. Control pigs had a total death loss of 12.2%. Death loss due to *E. coli* disease/scours was 9.4%. Treated pigs had a placement rate of 94.5% of animals into the finisher phase compared to control pigs which had a finisher placement of 87.9% (Table 14).

Three swabs were sent from treated pigs and three swabs were sent from control pigs. From the six swabs, 18 *E. coli* isolates were tested to determine their pathogenicity using the multiplex PCR procedure. The nine isolates that came from the three swabs obtained from the treated pigs were negative for pathogenic *E. coli*. Four of the nine isolates that came from the three swabs obtained from the control pigs were positive for the K88 pili gene and the Lt and Stb enterotoxin gene, as shown in Table 15. Therefore, the isolates from the control pigs were pathogenic *E. coli* and represented two of the three swabs taken from control pigs.

TABLE 14

Death causes during Field Trial D. Numbers represent the number of pigs that died due to that cause.

|  | Treated Pigs (received Product 3) | Control Pigs (did not receive Product 3) |
|---|---|---|
| Scour | 6 | 38 |
| Small | 1 | 1 |
| Very Small | 3 | 10 |
| Fighting | 1 | 0 |
| Flu/Respiratory | 2 | 0 |
| Not Eating | 1 | 0 |
| Gaunt | 1 | 0 |
| Not Sure | 3 | 0 |
| Total Death Loss | 18 | 49 |
| Total *E. coli*/Scour Loss | 6 | 38 |

TABLE 15

Characterization of *E. coli* isolates obtained from Field Trial D.

| Swab | Treated or Control Pigs | Multiplex Results on isolates obtained from swab |
|---|---|---|
| 1 | Treated | Negative for *E. coli* virulence factors |
| 2 | Treated | Negative for *E. coli* virulence factors |
| 3 | Treated | Negative for *E. coli* virulence factors |
| 4 | Control | Negative for *E. coli* virulence factors |
| 5 | Control | K88, LT, Stb |
| 6 | Control | K88, LT, Stb |

In Field Trial D, feeding Product 3 to nursery swine throughout the nursery period decreased mortality due to *E. coli* disease and increased the number of pigs placed in finisher.

Example 16

Field Trial E

The objective of Field Trial E was to evaluate the ability of the selected *Bacillus* strains to reduce the incidence of *E. coli* disease and to improve performance in the nursery phase.

The study site is located approximately 7 miles east of Pipestone, Minn. The cooperating producer's facility consists of approximately 450-500 sows of Babcock genetics and is a farrow to finish operation. Gilts typically enter farrowing at approximately 11 months of age and are taken through 5 farrowings. *E. coli* (F18) has been diagnosed on the farm with outbreaks occurring recently.

The nursery facility consists of six rooms with each room divided into one row of six pens. Each pen typically houses 25-35 pigs and pigs remain in the nursery on an average of 30 days before being moved to the finishing facility.

The pigs were weaned at 15 days of age and were sorted into one of three weight classes (light, medium, and heavy). Gilts and barrows were commingled within the same weight group in each of the pens. Ideally, the same weight group between the treated and control pens did not differ by more than 0.5 lbs.

A barrier was placed in between the two middle pens to divide the row into three pens of control and three pens of treated pigs. This barrier also minimized cross contamination between treated and control pigs.

The treated pigs received Product 3 as described in Example 15 in both the standard farm pellet diet and in the grind and mix diet at $7.35 \times 10^5$ cfu/g inclusion rate. The pellet diet was started on day one post-weaning, and Product 3 was continued in all diet phases until the end of the nursery stage. The control pigs received the same pelleted and grind and mix diets as the treated pigs except they were devoid of the Product 3 *Bacillus* strains. The control diet did contain another commercial *Bacillus* product in the pelleted rations and the first grind and mix ration. Egg immunoglobins were also included in the control pelleted rations.

Included in the nursery pellet diet for control and treated pigs was the antibiotic T135C400 (Denagard and chlortetracycline). Normal protocol was utilized for pig management.

Mortality and other clinical signs of disease were recorded in both the treated and control pens. Comments on cause of death were also recorded. Pigs were weighed by pen using the Transcell Technology TI-500SS B. Weights were collected at weaning (day 0), day 7, and day 28. The amount of feed fed was recorded daily, and on the last day of trial all the left over feed was weighed.

Rectal and fecal swabs were obtained from the nursery during an *E. coli* outbreak. *E. coli* strains were grown and isolated at Agtech Products and kept frozen for future use. Multiplex PCR was used to determine if a strain was pathogenic.

Data were analyzed using the PROC MIXED procedure of the SAS computer program, and the effects of block and treatment, with day included, to take into account repeated measures and interactions, were evaluated. Data is summarized in Table 16.

Figure 15A:
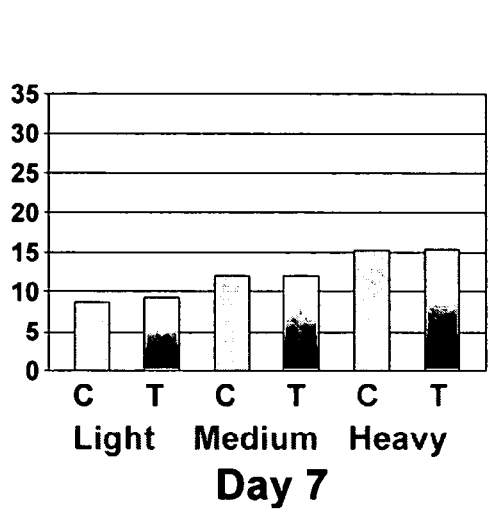
FIGS. 15A and 15B are graphs showing the effect of a preferred embodiment of a combination of *Bacillus* strains (Product 3) on pig weight for Field Trial E at Day 7 (FIG. 15A) and Day 15 (FIG. 15B).
Figure 15B:
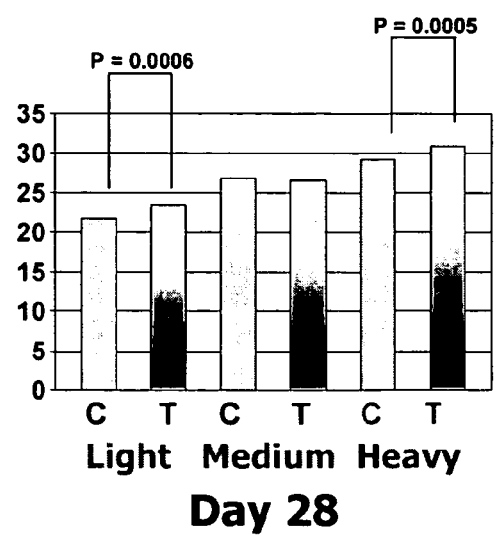

Referring to FIGS. 15A and 15B, pig weight was influenced by treatment ($P<0.01$), block ($P<0.0001$) and treatment×block ($P<0.01$) and block×day ($P<0.01$). Heavy and light pigs fed the *Bacillus* strains had higher body weights than pigs fed the control diet at day 28 ($P<0.005$ and $P<0.01$, respectively), as is shown in FIG. 15B.

Figure 16:
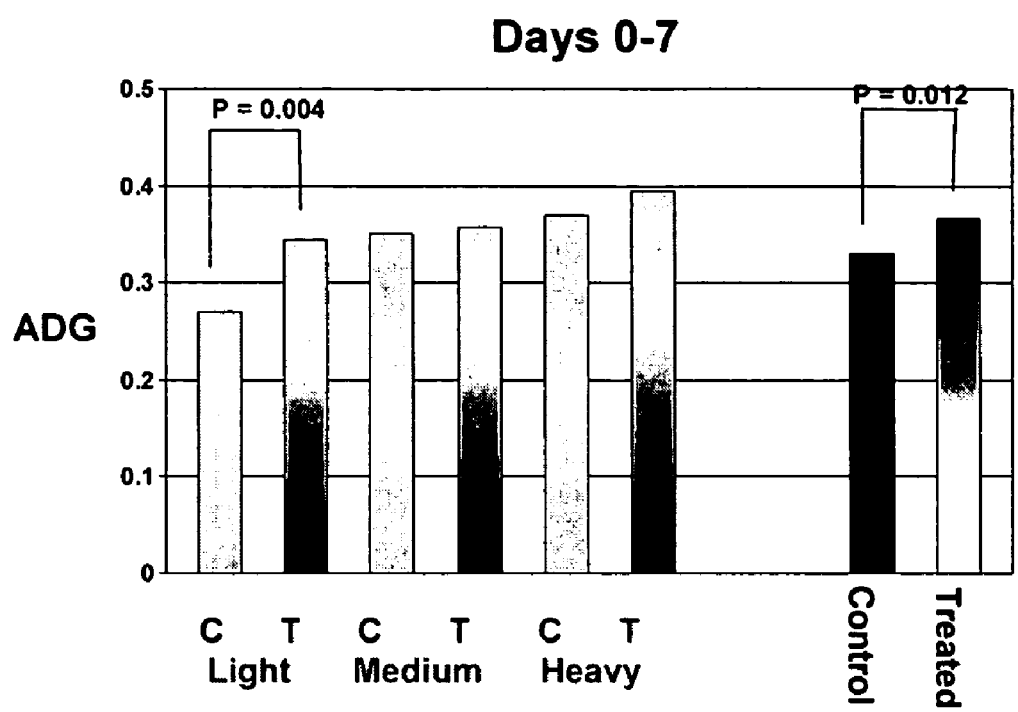
FIG. 16 is a graph showing the effect of Product 3 on ADG for Field Trial E.

Average daily gain for treated pigs was always higher than ADG for control pigs. For Day 0 to 7 all main effects and the rep×block ($P=0.0250$) interaction was significant (FIG. 16). The treatment×block interaction is approaching significance ($P=0.102$). Day 7 to 28 the effect of treatment was approaching significance ($P=0.125$). Day 0 to 28 all main effects were significant and the effect of treatment was nearly significant ($P=0.052$).

TABLE 16

Summary of the effect of Product 3 for Field Trial E.

| Day 28 | Treated n = 18 | Control n = 18 | % Difference |
|---|---|---|---|
| % Mortality | 1.5 | 3.5 | 57.1 |
| Weight/pig (lb) | 26.98 | 25.89 | 4.2 |
| ADG (lb/day) | | | |
| 0-7 | 0.37 | 0.33 | 12.1 |
| 7-28 | 0.70 | 0.66 | 6.1 |
| 0-28 | 0.62 | 0.58 | 6.9 |
| Feed:Gain | 1.34 | 1.42 | 5.6 |
| Gain:Feed | 0.745 | 0.711 | 4.8 |
| Feed Intake (lb) | 1927.17 | 1826.33 | 5.5 |

Figure 17:
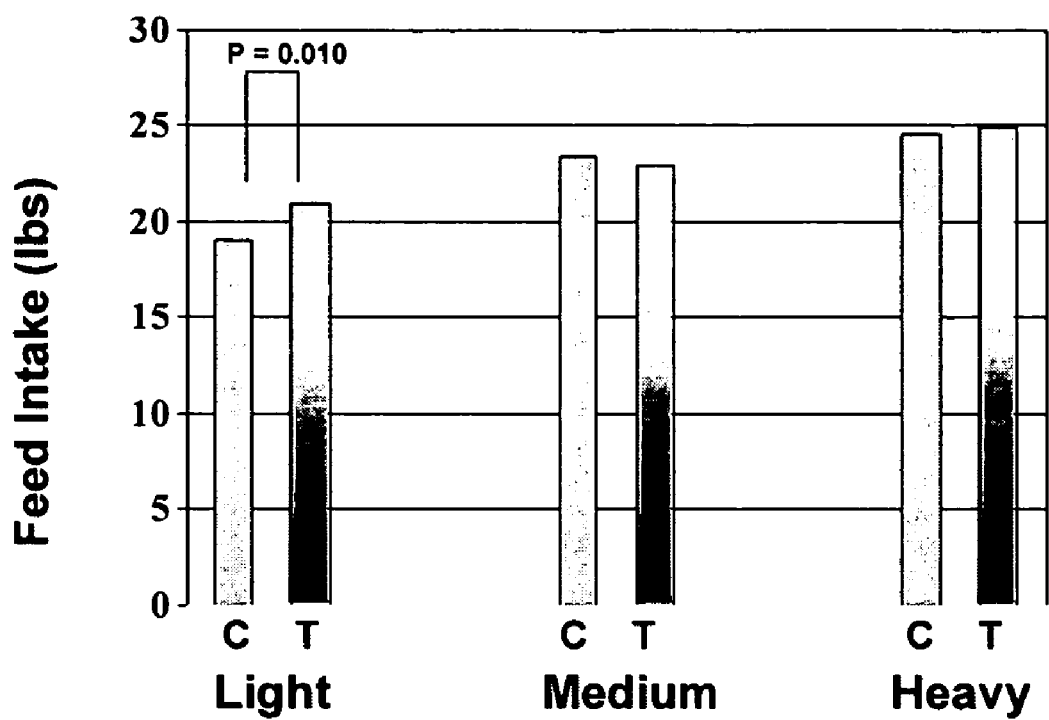
FIG. 17 is a graph showing the effect of Product 3 on feed intake for Field Trial E.

Feed intake (FIG. 17) in pigs in the light weight block was higher (P<0.01) whereas intake of pigs in the other blocks was similar (Treatment×block interaction, P<0.05).

The feed:gain effect of treatment was approaching significance (P=0.125).

Figures 18A, 18B:
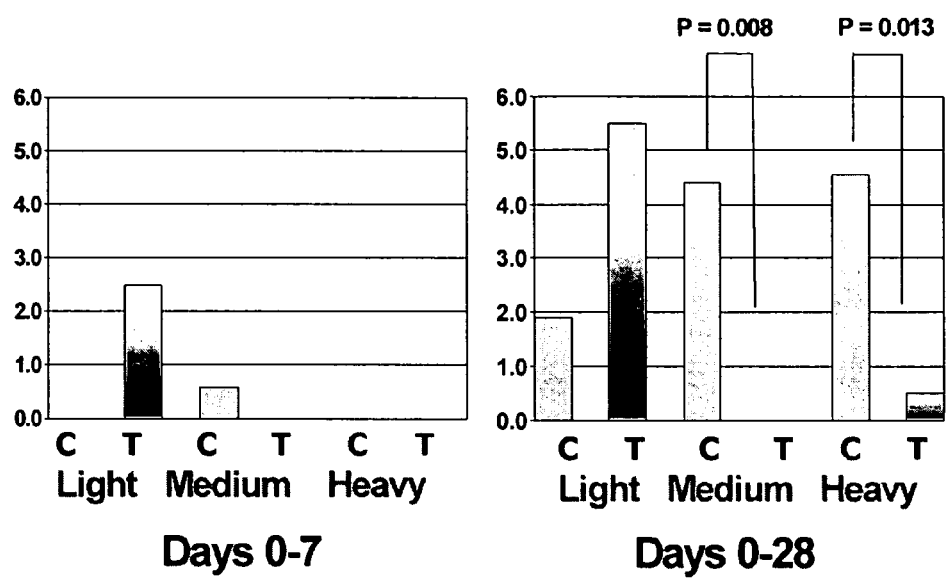
FIGS. 18A and 18B are graphs showing the effect of Product 3 on mortality for Field Trial E at Days 0-7 (FIG. 18A) and Days 0-28 (FIG. 18B).

Referring now to FIGS. 18A and 18B, feeding the *Bacillus* strains reduced mortality in the high (P<0.01) and medium (P<0.01) weight blocks at day 28 (Treatment×block×day interaction, P<0.05) (FIG. 18B).

Figure 19:
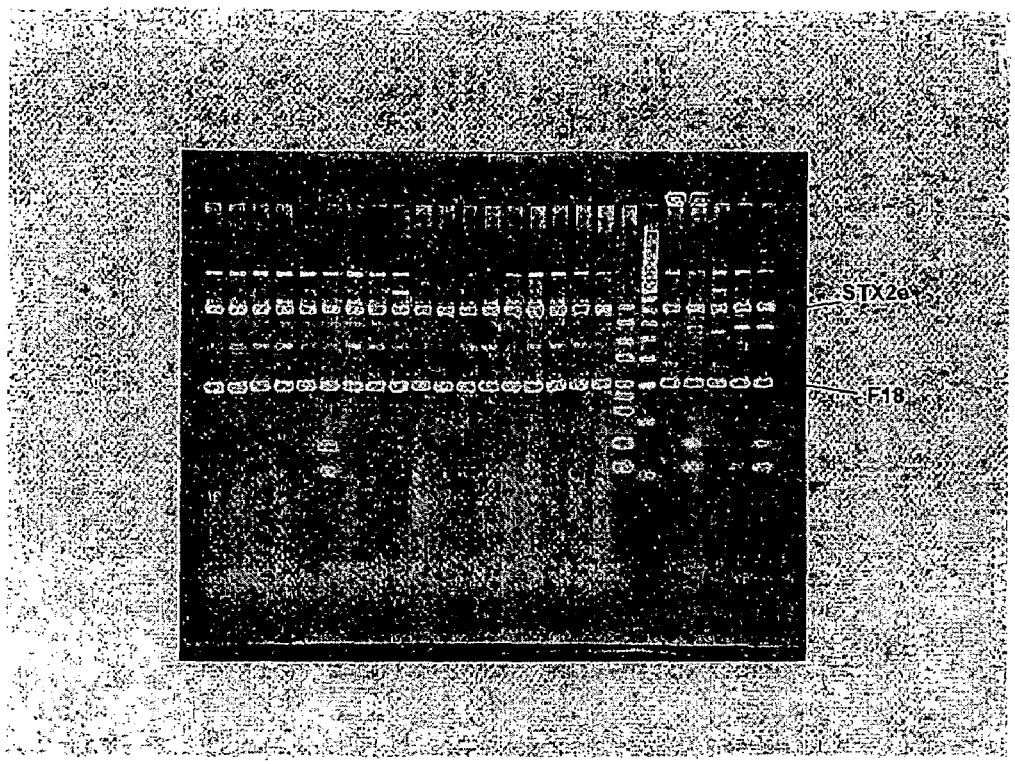
FIG. 19 is the multiplex results of Field Trial E.

Six swabs were sent from control pigs showing symptoms of *E. coli* edema disease. None of the treated pigs displayed any symptoms of *E. coli* disease. Therefore, no swabs from treated pigs were taken. From the six swabs 24 *E. coli* isolates were tested to determine their pathogenicity using the multiplex PCR procedure. All the isolates were positive for the F18 pili gene and Stx2e toxin gene, three isolates were positive for the Sta and Stb enterotoxin genes (FIG. 19). Therefore, all the isolates were positive for pathogenic *E. coli*, which accounted for the clinical signs manifested by the control pigs.

In Field Trial E, feeding Product 3 throughout the nursery period enhanced performance by increasing ADG, pig weight, feed intake, and feed conversion. Feeding Product 3 throughout the nursery period decreases mortality due to *E. coli* disease in Field Trial E.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. For example a single *Bacillus* isolate, as opposed to a combination of isolates, could be used to control pathogenic swine *E. coli*.

The invention is not intended to be limited to the preferred embodiments described above, but rather is intended to be limited only by the claims set out below. Thus, the invention encompasses all alternative embodiments that fall literally or equivalently within the scope of the invention.

BIBLIOGRAPHY

1. Dean-Nystrom, E. A. and Bartels-Morozov, D. 2001. Edema disease: a re-emerging problem. Proceedings of the American Association of Swine Veterinarians. 223-224.
2. Blood, D. C. and Radostits, O. M. Veterinary Medicine 7th Edition. 637-640.
3. Helman, R. Gayman. The Veterinary Clinics of North America Food Animal Practice. March 2000. 117-162.
4. Bertschinger, H. U. and Fairbrother, J. M. Diseases of Swine 8th edition. 431-454.
5. Gyles, C. 2001. *Escherichia coli* in Diseases of Weaned Pigs: Biological Aspect. American Association of Swine Veterinarians. 29-41.
6. Francis, D. H. 2004. Post-Weaning *E. coli*-diagnosis, treatment, control, and its effect on subsequent growth performance. American Association of Swine Veterinarians. 495-499.
7. Wills, R. W. Diarrhea In Growing-Finishing Swine. The Veterinary Clinics of North America. March 2000. 138-140.
8. Parrott, D., Rehberger, T. and Holt, M. 2002. Molecular typing of hemolytic *Escherichia coli* isolated from swine. Paper 385. International Pig Veterinary Society.
9. Marquardt, R. R., and et al. 1999. Passive protective effect of egg-yolk antibodies against enterotoxigenic *Escherichia coli* K88+ infection in neonatal and early-weaned piglets. FEMS Immunology and Medical Microbiology. 23. 1999. 283-288.
10. Nagy, B., Wilson, R., Whittam, T. Genetic diversity among *Escherichia coli* isolates carrying F18 genes from pigs with porcine postweaning diarrhea and edema disease. Journal of Clinical Microbiology. May 1999. 1642-1645.
11. Roe, S. Protein Purification Techniques. Second edition. 172-175.

What is claimed is:

1. An isolated microorganism of the genus *Bacillus* selected from the group consisting of strains 3A-P4 ATCC PTA-6506, 15A-P4 ATCC PTA-6507, and 22C-P1 ATCC PTA-6508.

2. The microorganism of claim 1, wherein the microorganism is capable of at least one of the following:
   (A) inhibiting *E. coli* disease in animals fed the microorganism when compared to animals not fed the microorganism, and
   (B) improving performance in animals fed the microorganism compared to animals not fed the microorganism, wherein the improvement in performance includes an improvement in at least one of average daily gain (ADG), weight, mortality, feed conversion, and feed intake.

3. The microorganism of claim 1, wherein the microorganism is strain 15A-P4 ATCC PTA-6507.

4. A combination of microorganisms comprising at least two microorganisms of claim 1.

5. The combination of claim 4, wherein the combination comprises strains 22C-P1 ATCC PTA-6508 and 15A-P4 ATCC PTA-6507.

6. The combination of claim 5, wherein the combination comprises 90% of the total count of strain 22C-P1 ATCC PTA-6508 and 10% of the total count of strain 15A-P4 ATCC PTA-6507.

7. The combination of claim 6, further comprising a feed, wherein the combination has a count of $5.1 \times 10^8$ CFU/g of feed.

8. The combination of claim 5, wherein combination comprises 10% of the total count of strain 22C-P1 ATCC PTA-6508 and 90% of the total count of strain 15A-P4 ATCC PTA-6507.

9. The combination of claim 8, further comprising a feed, wherein the combination has a count of $1 \times 10^6$ CFU/g of feed.

10. An isolated *Bacillus* strain 3A-P4 ATCC PTA-6506.

11. An isolated *Bacillus* strain 15A-P4 ATCC PTA-6507.

12. An isolated *Bacillus* strain 22C-P1 ATCC PTA-6508.

13. A combination of microorganisms of the genus *Bacillus*, the combination comprising strains 22C-P1 ATCC PTA-6508 and 15A-P4 ATCC PTA-6507.

14. A method of feeding swine, the method comprising feeding to the swine the microorganism of claim 1.

15. The method of claim 14, wherein the microorganism is strain 15A-P4 ATCC PTA-6507.

16. The method of claim 14, wherein the microorganism comprises at least two strains.

17. The method of claim 16, wherein the strains comprise strain 22C-P1 ATCC PTA-6508 and strain 15A-P4 ATCC PTA-6507.

18. The method of claim 17, wherein the microorganism comprise 90% of the total count of strain 22C-P1 ATCC PTA-6508 and 10% of the total count of strain 15A-P4 ATCC PTA-6507.

19. The method of claim 17, wherein the microorganism comprise 10% of the total count of strain 22C-P1 ATCC PTA-6508 and 90% of the total count of strain 15A-P4 ATCC PTA-6507.

20. A method of forming a direct-fed microbial, the method comprising:
   (a) growing, in a liquid nutrient broth, the microorganism of claim 1; and
   (b) separating the microorganism from the liquid to form the direct-fed microbial.

21. The method of claim 20, wherein the microorganism is strain 15A-P4 ATCC PTA-6507.

22. The method of claim 21, further comprising:
   growing, in a liquid broth, strain 22C-P1 ATCC PTA-6508; and
   combining strains 15A-P4 ATCC PTA-6507 and 22C-P1 ATCC PTA-6508.

23. A method of feeding swine, the method comprising feeding to the swine the combination of claim 13.

* * * * *

UNITED STATES PATENT AND TRADEMARK OFFICE
CERTIFICATE OF CORRECTION

PATENT NO.        : 7,618,640 B2                                               Page 1 of 1
APPLICATION NO. : 11/129767
DATED             : November 17, 2009
INVENTOR(S)       : Rehberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 639 days.

Signed and Sealed this

Fourteenth Day of December, 2010

David J. Kappos
*Director of the United States Patent and Trademark Office*